United States Patent
Seino et al.

(10) Patent No.: US 7,166,764 B2
(45) Date of Patent: Jan. 23, 2007

(54) NOC2 KNOCKOUT MOUSE

(75) Inventors: Susumu Seino, 3-11-405, Hunado-cho, Ashiya-shi, Hyogo 659-0093 (JP); Takashi Miki, Hyogo (JP); Toshihiko Iwanaga, Hokkaido (JP); Masanari Matsumoto, Chiba (JP)

(73) Assignees: JCR Pharmaceuticals Co., Ltd., Hyogo (JP); Susumu Seino, Hyogo (JP)

( * ) Notice: Subject to any disclaimer, the term of this patent is extended or adjusted under 35 U.S.C. 154(b) by 0 days.

(21) Appl. No.: 11/095,668

(22) Filed: Apr. 1, 2005

(65) Prior Publication Data

US 2006/0021073 A1  Jan. 26, 2006

(30) Foreign Application Priority Data

Apr. 2, 2004 (JP) ............ P2004-110374

(51) Int. Cl.
*A01K 67/00* (2006.01)
*G01K 33/00* (2006.01)
*C12N 5/08* (2006.01)
*C12N 15/00* (2006.01)

(52) U.S. Cl. .............. 800/18; 435/354; 800/3
(58) Field of Classification Search ............ 800/18, 800/25, 3; 435/325, 354
See application file for complete search history.

(56) References Cited

OTHER PUBLICATIONS

Keri et al, PNAS, 97(1): 383-387, 2000.*
Lariviere et al, J Pharm Exp Ther, 297(2): 467-473, 2001.*
Kotake et al, JBC, 272(47): 29407-29410, 1997.*
Capecchi et al, Scientific American, pp. 52-59, 1994.*
Jahn et al., "Membrane Fusion and Exocytosis," Annu. Rev. Biochem., 1999, vol. 68, pp. 863-911.
Rettig et al, "Emerging Roles of Presynaptic Proteins in Ca++-Triggered Exocytosis," Science, 2002, vol. 298, pp. 781-785.
Burgoyne et al., "Secretory Granule Exocytosis," Physiol. Rev., 2003, vol. 83, pp. 581-632.
Burgoyne et al., "Analysis of regulated exocytosis in adrenal chromaffin cells: insights into NSF/SNAP/SNARE Function," Bioessays, 1998, vol. 20, pp. 328-335.
Lang, "Molecular mechanisms and regulation of insulin exocytosis as a paradigm of endocrine secretion," Eur. J. Biochem., 1999, vol. 259, pp. 3-17.
Williams, "Intracellular signaling mechanisms activated by cholecytokinin-regulating synthesis and secretion of digestive enzymes in pancreatic acinar cells," 2001, Annu Rev. Physiol., vol. 63, pp. 77-97.
Takai et al., "Small GTP-Binding Proteins," Physiol. Rev., 2001, vol. 81, pp. 153-208.
Zerial et al., "RAB proteins as membrane organizers," Nat. Rev. Mol. Cell Biol., 2001, vol. 2, pp. 107-117.
Castillo et al., "Rab3A is essential for mossy fibre long-term potentiation in the hippocampus," Nature, 1997, vol. 388, pp. 590-593.

(Continued)

*Primary Examiner*—Deborah Crouch
*Assistant Examiner*—Magdalene K. Sgagias
(74) *Attorney, Agent, or Firm*—Millen, White, Zelano, Branigan, P.C.

(57) ABSTRACT

Disclosed are a mouse homozygous or heterozygous for the defect of the Noc2 gene, and a tissue and a cell of the mouse. The Noc2 knockout mice, which exhibit stress-related insulin hyposecretion and accumulation of secretory granules of increased size and irregular shape in exocrine cells, provide a test system used in the development of therapeutic drugs for related disorders.

10 Claims, 9 Drawing Sheets

OTHER PUBLICATIONS

Lledo et al., "Inhibition of Rab3B expression attenuates Ca2+-dependent exocytosis in rat anterior pituitary cells," Nature, vol. 364, Aug. 5, 1993.

Fischer et al., "Rab3C Is a synaptic vesicle protein that dissociates from synaptic vesicles after stimulation of exocytosis," R. J. Biol. Chem., 1994, vol. 269, No. 15, pp. 10971-10974.

Chen et al., "Dominant negative Rab3D inhibits amylase release from mouse pancreatic acini," 2002, vol. 277, No. 20, pp. 18002-18009.

Shirataki et al., "Rabphilin-3A, a putative target protein for smg p25A/rab3A p25 small GTP-Binding protein related to synaptotagmin," Molecular and Cell Biology, 1993, vol. 13, No. 4, pp. 2061-2068.

Wang et al., "Rim is a putative Rab3 effector in regulating synaptic-vesicle fusion," Nature, 1997, vol. 388, pp. 593-598.

Ozaki et al., "cAMP-GEFII is a direct target of cAMP in regulated exocytosis," 2000, Nat Cell Biol., vol. 2, pp. 805-811.

Kotake et al., "Noc2, a putative zinc finger protein involved in exocytosis in endocrine cells," The Journal of Biological Chemistry, 1997, vol. 272, No. 47, pp. 29407-29410.

Schoch et al., "Rim1α forms a protein scaffold for regulating neurotransmitter release at the active zone," Nature, 2002, vol. 415, pp. 321-326.

Castillo et al., "Rim1α is required for presynaptic long-term potentiation," Nature, 2002, vol. 415, pp. 327-330.

Koushika et al., "A post-docking role for active zone protein rim," Nat Neurosci., 2001, vol. 4, No. 10, pp. 997-1005.

Burns et al., "Rabphilin-3A: A multifunctional regulator of synaptic vesicle traffic," J Gen Physiol., 1998, vol. 111, pp. 243-255.

Schluter et al., "Rabphilin knock-out mice reveal that rabphilin is not required for Rab3 function in regulatin neurotransmitter release," The Journal of Neuroscience, Jul. 15, 1999, vol. 19, No. 14, pp. 5834-5846.

Kashima et al., "Critical role of cAMP-GEFII.Rim2 complex in incretin-potentiated insulin secretion," The Journal of Biological Chemistry, 2001, vol. 276, No. 49, pp. 46046-46053.

Fujimoto et al., "Piccolo, a Ca2+ sensor in pancreatic β-cells," The Journal of Biological Chemistry, Dec. 2002, vol. 277, No. 52, pp. 50497-50502.

Haynes et al., "A direct inhibitory role for the Rab3-specific effector, Noc2, in Ca2+- regulated exocytosis in neuroendocrine cells," The Journal of Biological Chemistry, 2001, vol. 276, No. 13, pp. 9726-9732.

De Boer et al., "Plasma catecholamine, corticosterone and glucose responses to repeated stress in rats: Effect of interstressor interval length," Physiology and Behavior, 1990, vol. 47, pp. 1117-1124.

Okabe et al., "Green mice' as a source of ubiquitous green cells," 1997, FEBS Letters, vol. 407, pp. 313-319.

Miki et al., "Defective insulin secretion and enhanced insulin action in $K_{ATP}$ channel-deficient mice," Proc. Natl. Acad. Sci. USA, Sep. 1998, vol. 95, pp. 10402-10406.

Ohnishi et al., "Overexpression of Rab3D enhances regulated amylase secretion from pancreatic acini of transgenic mice," 1997, J Clin Invest, vol. 100, No. 12, pp. 3044-3052.

Carrasco et al., "Neuroendocrine pharmacology of stress," 2003, vol. 463, pp. 235-272.

Lang et al., "Direct control of exocytosis by recptor-mediated activation of the heterotrimeric GTPases Gi and Go or by the expression of their active Gα subunits," The EMBO Journal, 1995, vol. 14, No. 15, pp. 3635-3644.

Renstroem et al., "Neurotransmitter-Induced inhibition of exocytosis in insulin-secreting β-cells by activation of calcineurin." Neuron, Sep. 1996, vol. 17, pp. 513-522.

Sharp et al., "Mechanisms of inhibition of insulin release," Am J. Physiol., 1996, vol. 271, pp. 1781-1799.

Yaekura et al., "Insulin secretory deficiency and glucose intolerance in Rab3A Null mice," Mar. 14, 2003, vol. 278, No. 11, pp. 9715-9721.

Naya et al., "Diabetes, defective pancreatic morphogenesis, and abnormal enteroendocrine differentiation in BETA2/NeuroD-deficient mice," Genes & Development, 1997, vol. 11, pp. 2323-2334.

Ohnishi et al., "Rab3D localizes to zymogen granules in rat pancreatic acini and other exocrine glands," Am J Physiol., vol. 271, G531-538.

Riedel et al., "Rab3D is not required for exocrine exocytosis but for maintenance of normally sized secretory granules," Molecular and Cellular Biology, Sep. 2002, pp. 6487-6497.

* cited by examiner

NOC2 KNOCKOUT MOUSE

FIELD OF THE INVENTION

The present invention relates to a Noc2 knockout mouse, more specifically to a mouse in which the Noc2 gene is disrupted and which exhibits stress-related hyposecretion of insulin.

BACKGROUND OF THE INVENTION

Regulated exocytosis is a key biological process in secretory cells, and has been extensively studied in neurons, which release neurotransmitters from their synaptic vesicles (1, 2). Many non-neuronal cells such as endocrine and exocrine cells contain secretory vesicles identified as dense-core vesicles, the contents of which exert a variety of biological effects (3). Secretory vesicle exocytosis occurs in the secretion of hormones in amine/peptide containing endocrine cells (4, 5), and in the secretion of digestive enzymes in exocrine cells (6).

Rab3, a subfamily of the small GTP-binding protein Rab family (7), plays an important role in the process of targeting, docking, priming and fusion in exocytosis (8). There are four isoforms (A–D) in the Rab3 family, all of which have been associated with regulated exocytosis (9–12). Several potential effectors of Rab3 have been identified, including rabphilin3 (13) and Rims (Rim1 and Rim2) (14, 15), and Noc2 (16). Rim1 and rabphilin3 expressed predominantly in the brain (13, 14), suggesting their involvement in synaptic vesicle exocytosis. While it is suggested, through studies of Rim1-deficient (Rim1$^{-/-}$) mice and Caenorhabditis elegans, that Rim1 is involved in priming of synaptic vesicles (17–19), the role of rabphilin3 in synaptic vesicle exocytosis is not clear (20, 21).

Both Rim2 (15) and Noc2 (16) are expressed predominantly in neuroendocrine and endocrine cells (16), suggesting their involvement in secretory granules exocytosis (3). We have previously shown that Rim2, interacting with cAMP-GEFII (Epac2) and Piccolo, is responsible for cAMP-dependent, protein kinase A (PKA)-independent exocytosis of insulin granules (15, 22, 23).

The physiological function of Noc2 in exocytosis, however, remains unclear. By overexpressing Noc2 in PC12 cells, we and another group separately have found that Noc2 has positive (16) and negative (24) effects on $Ca^{2+}$-triggered exocytosis.

SUMMARY OF THE INVENTION

Against the above-mentioned background, the objectives of the present invention are to generate a Noc2 knockout mouse (Noc2$^{-/-}$), which serves as a tool of directly identifying the physiological role of Noc2, and to provide a model animal useful in the study of the cause of, and in the development of means for the treatment of, endocrine-related diseases, in particular insulin hyposecretion, based on findings obtained with such mice.

Thus, the present invention provides mice that are homozygous for the defect of the Noc2 gene, in which mice thereby no functional Noc2 is produced. In the course of analysis of physiological activities of those mice, it was found that while the mice exhibit, under normal conditions, a normal response of insulin secretion, and normal blood glucose levels as well, after a glucose load, they, under stressful conditions, show lowered response of insulin secretion after a glucose load, leading to elevation of blood glucose levels. The mice, therefore, can be used as an in vivo test system useful both in the investigation of the mechanism of stress-related insulin hyposecretion and in the development of therapeutic drugs for it. The mice also provide a test system for elucidating of the mechanism of, and development of therapeutic drugs of, insufficiency of external secretion, for they also have deficiency of external secretion.

The present invention further provides mice that are heterozygous for the defect of the Noc2 gene. The mice may be used not only as means for reproduction of mice that are homozygous for the defect of the Noc2 gene, through their cross-fertilization and examination of the presence/absence of the Noc2 gene product, but also for the same purpose as the homozygous mice as they themselves have at least a potential defect concerning insulin secretion and external secretion under stressful conditions.

The present invention also provides tissues of mice that are mono- or heterozygous for the defect of the Noc2 gene. Such tissues, for example pancreatic islets of homozygous animals, may be used as an in vitro test system for the development of therapeutic drugs for stress-induced insulin hyposecretion, for their insulin secretion is inhibited under stressful conditions.

The present invention also provides cells of mice that are homo- or heterozygous for the defect of the Noc2 gene. Such cells, e.g., pancreatic β-cells, may be used, like pancreatic islets, as an in vitro test system for the development of therapeutic drugs for stress-induced insulin hyposecretion. Further, germ cells or fertilized eggs of mice that are homozygous for the defect of the Noc2 gene can be used for the production of mice that are homozygous for the defect of the Noc2 gene.

The present invention provides in vivo and in vitro test systems used for the investigation of mechanisms causing abnormalities in endocrine and exocrine systems, and in the development of therapeutic drugs for such abnormalities.

DETAILED DESCRIPTION OF THE INVENTION

In the present invention, "defect of the Noc2 gene" means that no functional Noc2 protein is produced due to the disruption of the Noc2 gene.

As to the mice of the present invention, the term "tissue" includes any tissues, for example but not limited to, endocrine tissues such as pancreatic islets, pituitary glands and exocrine tissues such as exocrine pancreas, gastric glands, small intestinal glands, Brunner's glands, salivary glands, mammary glands, etc., and their acini.

When used concerning the mice of the present invention, the term "cells" includes any somatic and germ cells, including, for example but not limited to, cells forming endocrine and exocrine tissues such as pancreatic β-cells, acinar cells such as pancreatic acinar cells, as well as fertilized eggs and germs cells such as spermatozoa and ova.

EXAMPLE

As described below, the present inventors created Noc2 knockout mice and examined their physiological characteristics.

1. Generation of Noc2 Knockout Mice (Noc2$^{-/-}$)

Figure 1:
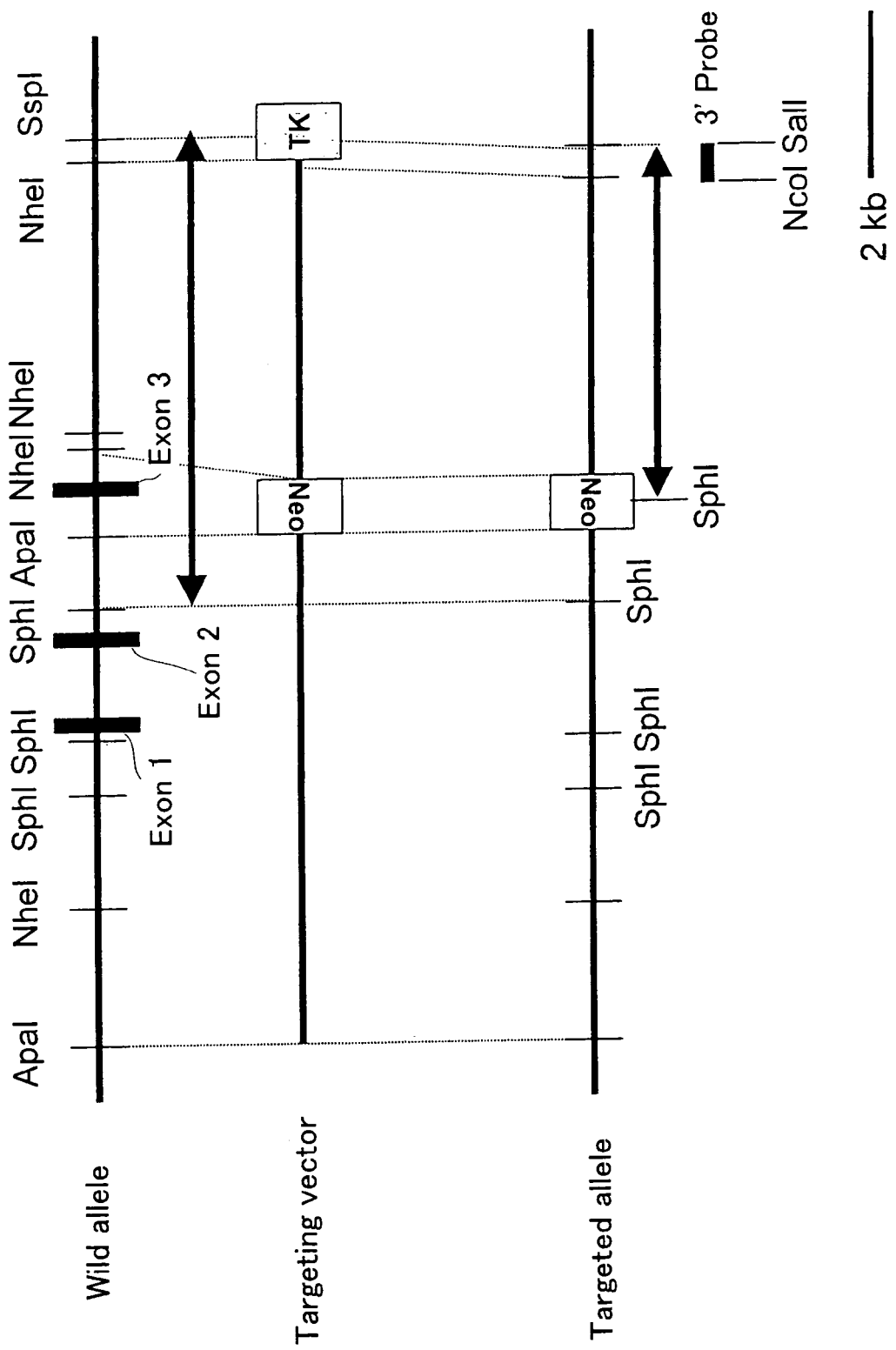
FIG. 1 shows a schematic diagram illustrating the method of preparing the targeting vector.

Noc2$^{-/-}$ Mouse Gene Targeting:

The present inventors generated Noc2 mice by replacing an exon 3-containing portion of Noc2 gene ranging from part of intron 2 to part of intron 3 (FIG. 1). Briefly, 129Sv mouse genomic library (in λDASH phage library) was screened using a full-length cDNA of the rat Noc2 coding region (SEQ ID NO:1)(nucleotides 1–1934). Nine positive clones were isolated, of which restriction maps were provided by combination of their digestion with restriction enzymes and Southern blotting using a rat Noc2 full-length cDNA as a probe. More specifically, a search performed in the GenBank database using the rat Noc2 full-length cDNA as a probe gave the genomic sequence coding for the mouse Noc2 gene (SEQ ID NO:2) (nucleotides 1–20492). By comparing the restriction maps of the nine genomic clones with the sequence data, a restriction map of about 15 kb was provided which covered from exon 1 to exon 3 (FIG. 1).

Based on the restriction map thus provided, a targeting vector was constructed by replacing a portion ranging from about 0.5 kb upstream of exon 3 of the mouse Noc2 gene to about 0.5 kb downstream of exon 3 (which region included introns 2 and 3 in part and exon 3) with a neomycin-resistant gene cassette, with a fragment ranging from the ApaI site within the promoter about 6 kb upstream of exon 3 of the mouse Noc2 gene to the ApaI site in intron 2 about 0.5 kb upstream of exon 3 employed as the 5' arm, and with a fraction ranging from the NheI site about 0.5 kb downstream of exon 3 of the mouse Noc2 gene to the NheI site about 3.8 kb downstream of exon 3 employed as the 3' arm. For negative selection, thymidine-kinase cassette was added to the 3' end of the targeting vector.

Briefly, a portion ranging from the ApaI site within the promoter about 6 kb upstream of exon 3 to the ApaI site within intron 2 about 0.5 kb upstream of exon 3 was cut out, blunt ended and subcloned into the PvuII site of pSP72. Selection was made for those having the insert cloned in the inverse direction relative to the plasmid. The cloned DNA was ring-opened with XhoI, and a SalI-XhoI fragment coding for neomycin-resistance gene cassette was inserted. The clone thus constructed was digested with SalI and XhoI to cut out the insert (referred to as "5'-arm+Neo"). In parallel, a fragment ranging from the NheI site about 0.5 kb downstream of exon 3 of the mouse Noc2 gene to the NheI site about 3.8 kb downstream of exon 3 (referred to as "3'-arm") was subcloned in the XbaI site of pGEM3z. Selection was made for those having the insert cloned in the inverse direction relative to the plasmid. To the SalI site of the clone was inserted the SalI-XhoI fragment of the "5'-arm+Neo" mentioned above, and then the SalI-XhoI fragment coding for a thymidine kinase gene cassette was inserted utilizing the SalI site. Linearization by SalI digestion gave the targeting vector.

The targeting vector was introduced into an ES cell line (R1) by electroporation and 414 viable clones were collected 8 days after the transfection. Clones in which homologous recombination had taken place were identified by Southern blotting (data not shown). Briefly, a 1.0 kb genomic fragment (NcoI-SalI fragment) downstream of the 3'-arm of the targeting vector was employed as a probe, and the genomic DNA was digested with EcoRI. Homologous recombination was found to have taken place in an ES cell clone. Using this clone, chimeric mice were generated through a cell aggregation process and a mouse line was established. Disruption of the Noc2 gene was identified by genomic Southern blotting and Northern blotting. Those mice were backcrossed with C57/BL6 mice.

Homozygous (Noc2$^{-/-}$) knockout mice were produced by crossing heterozygous (Noc2$^{+/-}$) mice. Homologous recombination was confirmed as described below by Southern blotting of genomic DNA isolated from the tail of the mice.

Figure 2:
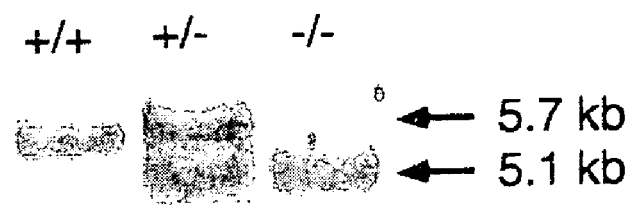
FIG. 2 shows a result of a Southern blot analysis of the mice.
Figure 3:
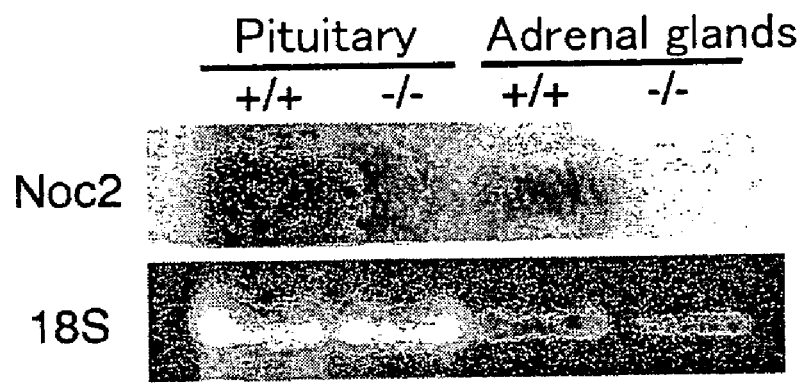
FIG. 3 shows a result of a Northern blot analysis of Noc2 mRNA from the pituitary and adrenal glands of wild-type and knockout mice.
Figure 4:
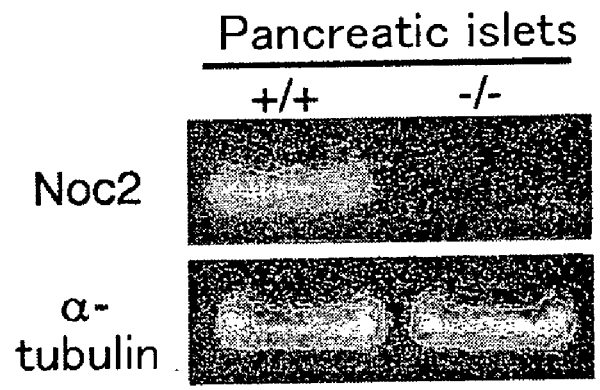
FIG. 4 shows a result of RT-PCR of Noc2 and α-tubulin of mouse pancreatic islets.

As a result, as shown in FIG. 2, it was found that a band corresponding to 5.7 kb disappeared in Noc2$^{-/-}$ mice and, instead, a band corresponding to 5.1 kb appeared. Only a band corresponding to 5.7 kb was detected in wild-type mice (Noc2$^{+/+}$), and both bands corresponding to 5.7 kb and 5.1 kb were detected in Noc2$^{+/-}$ mice. Lack of expression of Noc2 mRNA was also confirmed as described below. As shown in FIG. 3, Noc2 mRNA detected in pituitary and adrenal glands of wild-type mice was not detected in Noc2$^{-/-}$ mice. RT-PCT was carried out for the Noc2 gene transcription product as described below using total RNAs from pancreatic islets of Noc2$^{-/-}$ mice and wild-type mice, respectively. As shown in FIG. 4, no Noc2 gene transcription product was detected in Noc2$^{-/-}$ mice.

Methods of Southern Blotting, Northern Blotting and RT-PCT:

Genomic DNA (for Southern blotting) and total RNA (for Northern blotting) were prepared from the tail and various tissues of the mice by a standard method.

The genomic DNA was digested with SspI and SphI. The DNA (10 µg) or RNA (20 µg) was electrophoresed in a 1% agarose gel and then transferred to a nylon membrane. Under a highly stringent condition, hybridization was allowed with a $^{32}$P-labeled probe. The probe used in the Southern blotting was a genomic fragment of the indicated Noc2 (NcoI-SalI fragment)(SEQ ID NO:3). The probe used in the Northern blotting was a cDNA fragment of mouse Noc2 (SEQ ID NO:4) corresponding to nucleotides 1–994

(which included nucleotides 1–41 in the 5' untranslated region and nucleotides 948–994 in the 3' untranslated region).

The probe used in the Northern blotting was PCR amplified applying two primers, 5'-CGAAGCAGATGTGACTC-CTG-3' (SEQ ID NO:5) and 5'-TTCTGGAAGAGTTTGC-CTCA-3' (SEQ ID NO:6) to the both ends of the above-mentioned mouse Noc2 cDNA fragment. The probe was used after agarose electrophoresis, cutting out of the corresponding band, and purification. The mouse Noc2 cDNA fragment was prepared by PCR amplification using as a template a cDNA prepared from RNA extracted from MIN6 cells, which is a mouse pancreatic β-cell line, and the above-mentioned two primers, followed by subcloning into pGEM-T easy vector.

RT-PCT was carried out using the total RNA (10 μg) from pancreatic islets. The expected size of the PCR product was 345 bp. The PCR was carried out 30 cycles. The primers used for the PCR amplification were 5'-GCAGTGGAAAT-GATCAGTGG-3' (SEQ ID NO:7), a forward sequence of Noc2, and 5'-CATCACGTTCCTCTGCATTG-3' (SEQ ID NO:8), a reverse sequence.

2. Generation of Chimeric Mice from Noc2 Knockout and Normal Mice

By a conventional method, chimeric mice were generated by aggregating the 4 cell-stage fertilized eggs from $Noc2^{-/-}$ parents and those from wild-type ($Noc2^{+/+}$) parents expressing the green fluorescent protein (GFP) of a jellyfish, Aequorea victoria. Chimerism was determined by PCR or genomic Southern blot analysis. The wild-type eggs expressing GFP were prepared using male transgenic (homozygous for the transgene) mice expressing GFP under the control of CAG promoter (26). Briefly, a cDNA coding for an enhanced GFP (enhanced green fluorescent protein: EGFP), which was one of many classes of GFP mutants, was amplified by PCR in a conventional manner. The EcoRI sites included in the PCR primers were used to introduce the amplified EGFP cDNA into a pCAGGS expression vector containing the chicken beta-actin promoter and cytomegalovirus enhancer, beta-actin intron and bovine globin poly-adenylation signal. The entire insert with the promoter and coding sequence was excised with BamHI and SalI and purified. GFP transgenic mouse lines were generated by injecting the purified fragment into wild-type Noc2 mouse fertilized eggs, which were then transplanted to surrogate mothers and allowed to develop. One-day-old pups were examined under fluorescent microscope for expression of GFP, and those expressing GFP were selected.

3. Method of In Vivo Animal Experiment

Oral glucose tolerance test was performed on male 12–20 week-old mice fasted for 16 hours. Water immersion stress experiment was performed as previously described (25), using mice that were immobilized individually in a restraint holder and vertically immersed for 15 minutes in water at 20° C. (5 cm deep) after glucose load. Blood glucose levels were measured in whole blood with Antosense Glucose II (SANKYO). Serum insulin levels were determined by Ultra-high Sensitivity Rat Insulin ELISA kit (MORINAGA).

4. Measurement of Insulin Release from Isolated Pancreatic Islets

Pancreatic islets were isolated by collagenase digestion method in a conventional manner (27). The pancreatic islets were cultured for 48 hours in RPMI1640 medium in the presence or absence of PTX (30 ng/ml). Batch incubation was performed as previously described (27). Insulin released into the medium was measured by radioimmunoassay (EIKEN CHEMICAL). Recombinant adenoviruses carrying either LacZ, Noc2 wt (wild-type), or Noc2AAA (mutant) cDNA were generated according to the manufacturer's instructions (STRATAGENE). For preparation of Noc2AAA, Trp-Phe-Tyr (residues 154–156) were replaced with three alanine residues as previously described (24). The pancreatic islets of $Noc2^{-/-}$ mice were infected for 48 hours with one of these adenoviruses immediately after isolation. Lysate from COS-1 cells transfected with a Flag-tagged Rab3 isoforms was evaluated for binding to the GST-Noc2 wild-type (Noc2 wt) or the GST-Noc2 mutant (Noc2AAA) in the presence of GTP-γS.

Insulin secretion experiments were also performed using freshly prepared pancreatic islets without culture.

5. Measurement of Amylase Secretion from Isolated Pancreatic Acinar Cells

Pancreatic acini were prepared by collagenase digestion method. Amylase secretion experiments were performed according to Ohnishi et al. (28) with slight modifications. Briefly, isolated acini were suspended in an incubation buffer [consisting of 10 mM HEPES (pH 7.4), 127 mM NaCl, 4.7 mM KCl, 0.6 mM $MgCl_2$, 1.3 mM $CaCl_2$, 0.6 mM $Na_2HPO_4$, 2.0 mg/ml glucose, Eagle's MEM amino acids supplement, 2 mM L-glutamine, 1% BSA, 0.01% soybean trypsin inhibiter] as previously described (28) and preincubated at 37° C. for 30 minutes. After preincubation, the acini were centrifuged, resuspended in fresh incubation buffer, and incubated at 37° C. in the presence or absence of 30 pM CCK or 1 μM carbachol. Amylase released into the supernatant during incubation was quantified using Amylase B-test WAKO (WAKO PURE CHEMICAL INDUSTRIES). Amylase secretion was normalized as the amount released into the medium relative to the total amylase content in the pancreatic acinar cells (expressed as % amylase release).

6. In Vitro Binding Assay

Wild type Noc2 and mutant Noc2 (Noc2AAA), both full-length, were expressed as GST-fusion proteins and purified according to the manufacturer's instructions (AMERSHAM). Full-length Rab3A, B, C and D and Rab5 cDNAs were subcloned into pFLAG-CMV-2 (SIGMA). For cosedimentation assays, COS-1 cells were transfected with each of the plasmids using LipofectAMINE (INVITROGEN). Following the transfection, the cells were sonicated in a buffer [20 mM HEPES, pH 7.4, 200 mM NaCl, 1 mM dithiothreitol, 5 mM $MgCl_2$, 1 mM ATP and 0.26% (v/v) CHAPS]. In vitro binding assay was performed as previously described (15). Briefly, lysates from COS-1 cells transfected with FLAG-tagged Rab3 isoforms and Rab5 were assessed for binding to GST-Noc2 immobilized on glutathione beads in the presence of GDP-βS or GTP-γS. Rab3 isoforms and Rab5 and GST-Noc2 were detected by immunoblotting with anti-Flag antibody or immunoglobulin G-purified antibody against rat Noc2.

7. Histological Analysis

The pancreas and various portions of the gastrointestinal tract were removed from wild-type and $Noc2^{-/-}$ mice, and were immersion-fixed in 4% paraformaldehyde in 0.1 M phosphate buffer, pH 7.4. The fixed tissues then were dehydrated and embedded in paraffin by a conventional procedure. Five-μm thick paraffin sections were stained with hematoxylin and eosin (HE), Azan or periodic acid Schiff (PAS) for secretory granules, and immunostained for pancreatic hormones. Small tissue pieces from the pancreas, stomach and salivary glands were post-fixed with 2.5% glutaraldehyde and 1% $OsO_4$ and embedded in an epoxy resin. Semi-thin and ultra-thin sections were stained with toluidine blue and uranyl acetate/lead citrate for observation under light and electron microscopes, respectively.

[Results]

Figure 5:
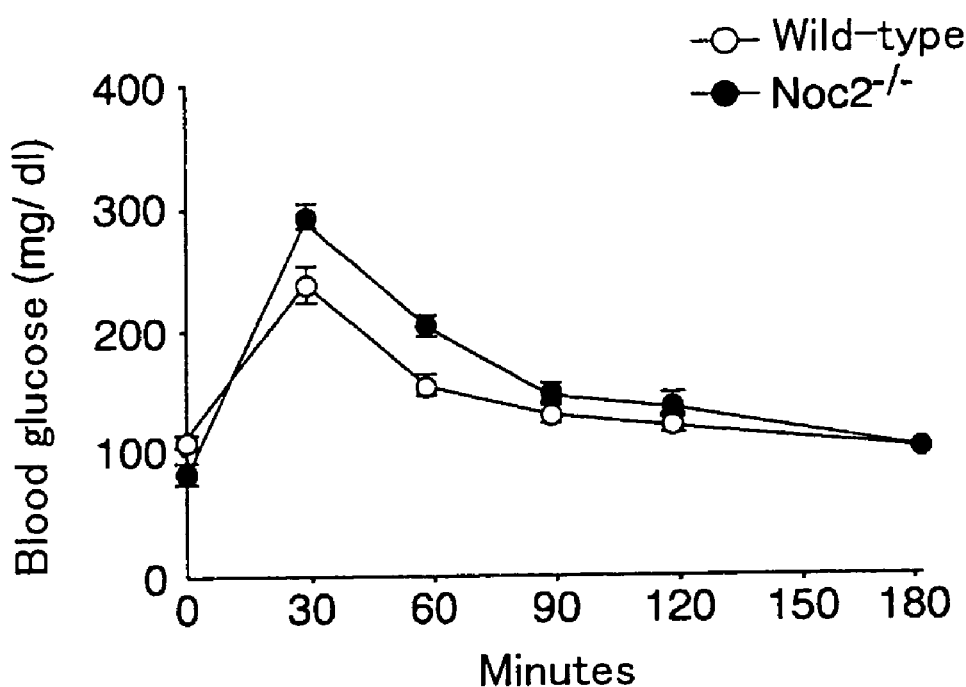
FIG. 5 is a graph showing the profiles of blood glucose levels in mice after oral glucose load.
Figure 6:
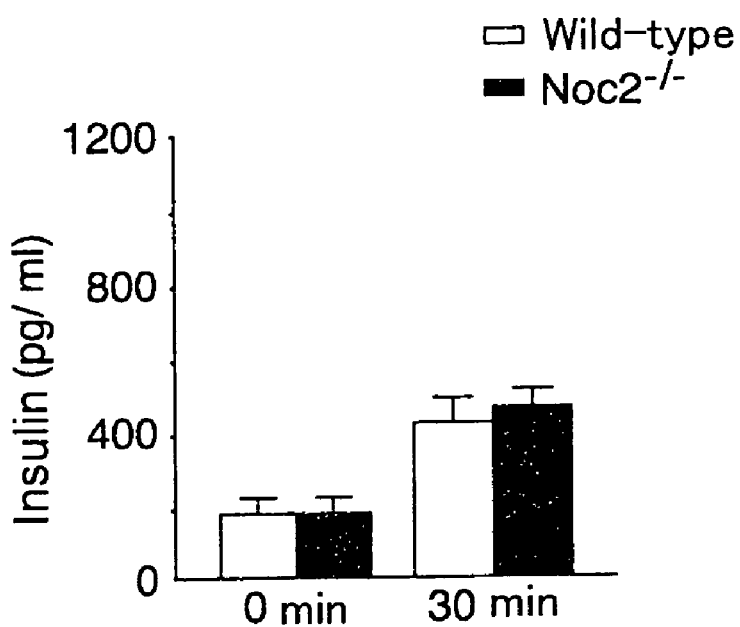
FIG. 6 is a graph showing the changes in blood insulin levels in mice after oral glucose load.

Disruption of the Noc2 gene was confirmed by a Northern blot analysis or reverse transcriptase-polymerase chain reaction (RT-PCR) analysis of total RNA from pituitary gland, adrenal glands and pancreatic islets. $Noc2^{-/-}$ mice developed normally and were fertile, with no abnormalities in general appearance or behavior. As Noc2 is expressed at high levels in endocrine tissues such as pancreatic islets (16), we first examined endocrine pancreatic function. $Noc2^{-/-}$ mice and Noc2 wild-type mice were comparable in blood glucose and serum insulin levels after oral glucose load under normal conditions, showing no statistical difference when small blood samples were taken (FIGS. 5 and 6, respectively). However, when a large amount of the blood was withdrawn, we incidentally found that while wild-type mice exhibited normal glucose levels and normal insulin response after glucose load, $Noc2^{-/-}$ mice exhibited significantly higher blood glucose levels with reduced insulin response compared to wild-type mice (data not shown).

Figure 7:
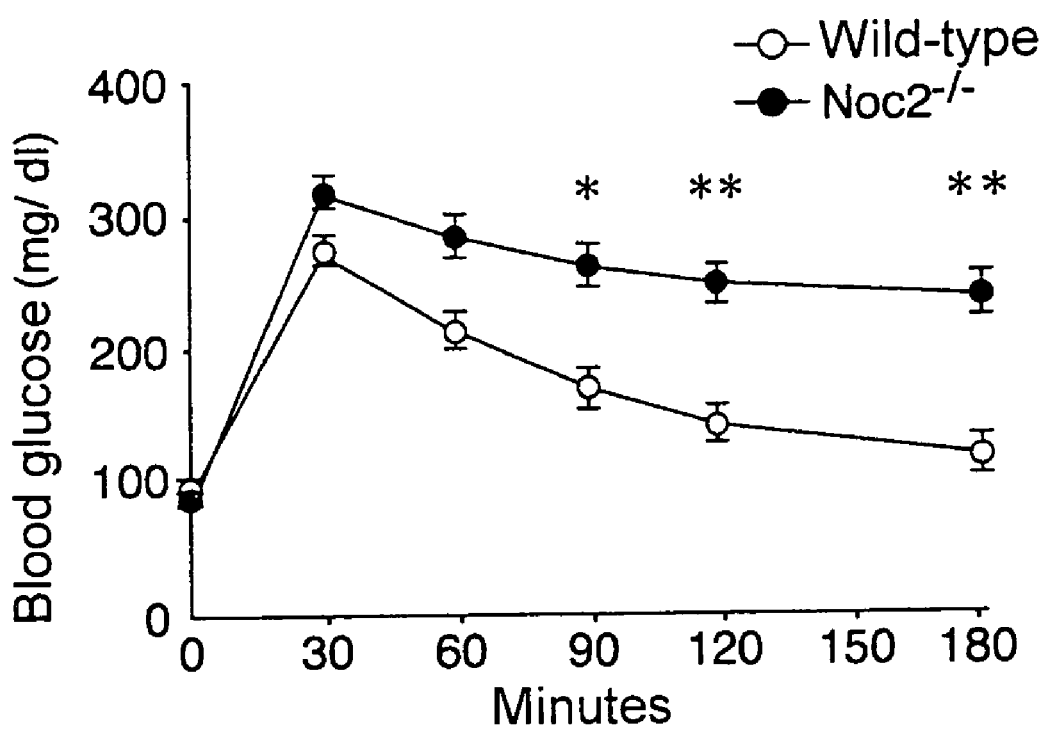
FIG. 7 is a graph showing the profiles of blood glucose levels in mice after oral glucose load under a water-immersion stress condition.
Figure 8:
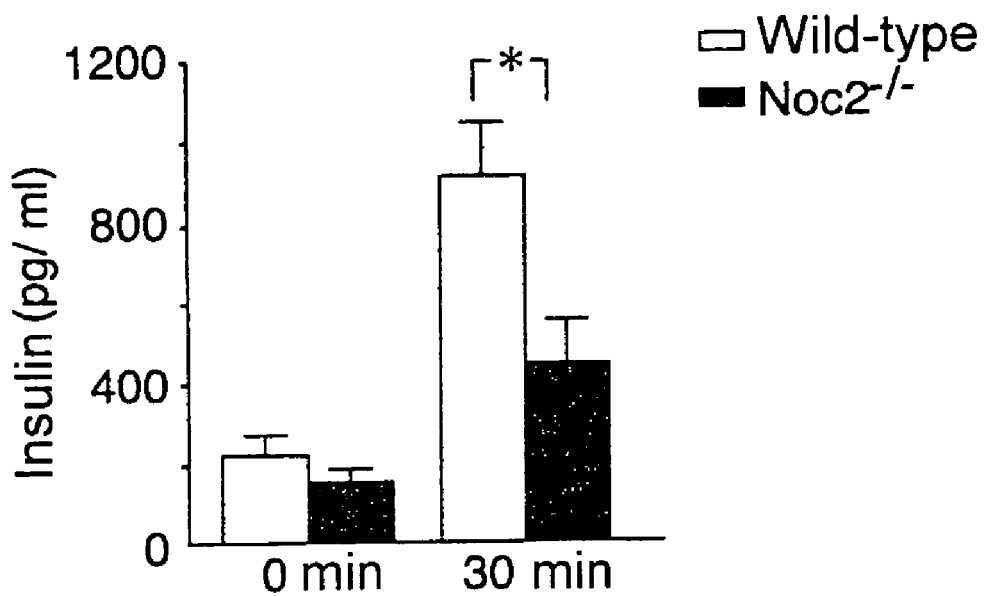
FIG. 8 is a graph showing the changes in blood insulin levels in mice after oral glucose load under a water-immersion stress condition.

A large amount of blood loss is known to elicit various stress responses (29). Thus, to investigate the response of endocrine pancreas in $Noc2^{-/-}$ mice to stress, blood glucose response and insulin response were measured under a water immersion stress (25). Water immersion stress elicited a sustained rise in blood glucose levels and markedly reduced insulin secretion in Noc2 mice after oral glucose load, but not in wild-type mice (FIGS. 6 and 7, respectively). Briefly, blood glucose levels at 90 min, 120 min and 180 min after glucose load were significantly higher in $Noc2^{-/-}$ mice than in wild-type mice (n=13 at each point, *p<0.01 at 90 min, **p<0.001 at 120 and 180 min.), and serum insulin levels at 30 min after glucose load were significantly lower in $Noc2^{-/-}$ mice than in wild-type mice (919.5±123.8 pg/ml for wild-type mice, n=22; 451.7±101.9 pg/ml for $Noc2^{-/-}$ mice, n=22, p<0.001). This indicates that wild-type mice can maintain normal blood glucose levels in response to water immersion stress by enhancing insulin secretion, while $Noc2^{-/-}$ mice cannot.

Figure 9:
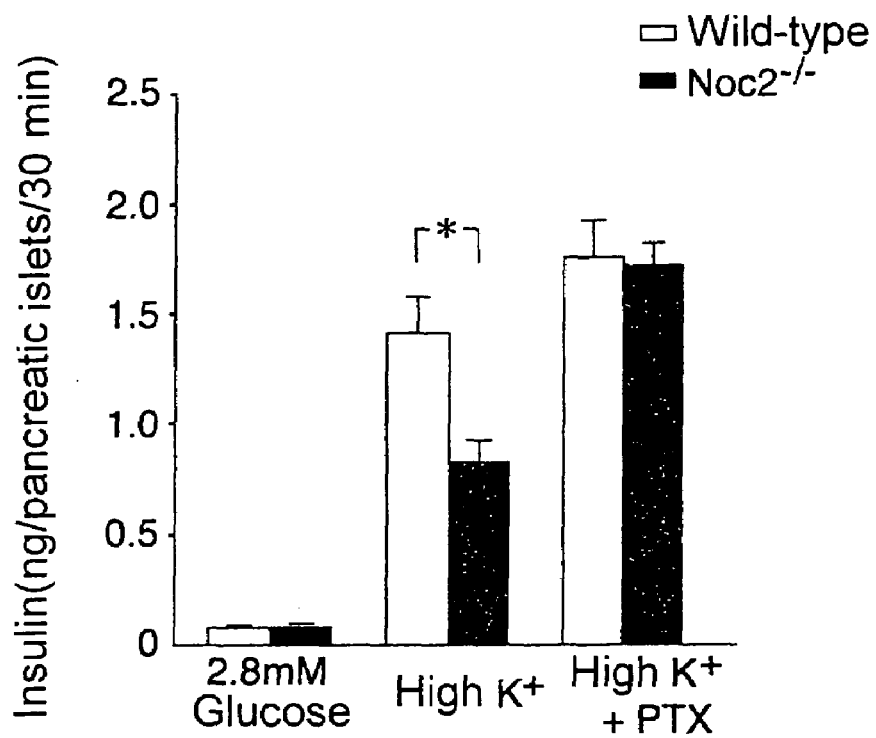
FIG. 9 is a graph showing the changes in the amount of insulin that was secreted by mouse pancreatic islets cultured for 24 hours after isolation.

As water immersion stress is known to trigger adrenergic response (25), and activation of inhibitory G-protein Gi/o signaling through $\alpha_2$-adrenergic receptors in pancreatic β cells inhibits insulin secretion (30–32), the defective insulin response in $Noc2^{-/-}$ mice in vivo might be associated with activation of Gi/o signaling in pancreatic βcells. In order to investigate the mechanism underlying defective insulin secretion in $Noc2^{-/-}$ mice, we examined insulin secretion in isolated pancreatic islets. As shown in FIG. 9, $Ca^{2+}$-triggered insulin secretion (assessed by high $K^+$ stimulation) markedly decreased in pancreatic islets cultured 24 hours after isolation from $Noc2^{-/-}$ mice. While there was no difference in insulin secretion at 2.8 mM glucose (basal state), high $K^+$ (60 mM)-induced insulin secretion in $Noc2^{-/-}$ mice was significantly lower than in wild-type mice (1.43±0.16 ng/islet/30 min for wild-type mice; 0.83±0.10 ng/islet/30 min for $Noc2^{-/-}$ mice, *p<0.0001). There was no difference in high $K^+$-induced insulin secretion between wild-type mice and $Noc2^{-/-}$ mice when the pancreatic islets were treated with PTX (30 ng/ml, 48 hours) after isolation (open circles and open columns; wild-type mice, filled circles and filled columns; $Noc2^{-/-}$ mice, values are means±s.e.m.).

In order to determine if the reduced insulin secretion in $Noc2^{-/-}$ mice is due to activation of Gi/o signaling, we examined the effect of PTX, which blocks Gi/o signaling, on $Ca^{2+}$-triggered insulin secretion. PTX treatment (48 hours) of pancreatic islets completely restored the once reduced $Ca^{2+}$-triggered insulin secretion in Noc2' mice. In contrast to the results obtained in the cultured pancreatic islets, $Ca^{2+}$-triggered insulin secretion in pancreatic islets was comparable between those freshly prepared from $Noc2^{-/-}$ mice and wild-type mice (data not shown). This difference between cultured pancreatic islets and freshly prepared ones suggests that Gi/o signaling is activated in $Noc2^{-/-}$ islets during culture (mechanism unknown). These results demonstrate that Noc2 is required in the maintenance of normal insulin secretion by inhibiting Gi/o signaling in pancreatic β cells. Disruption of Noc2 unmasks the Gi/o signal, thereby suppressing insulin secretion.

Figure 10:
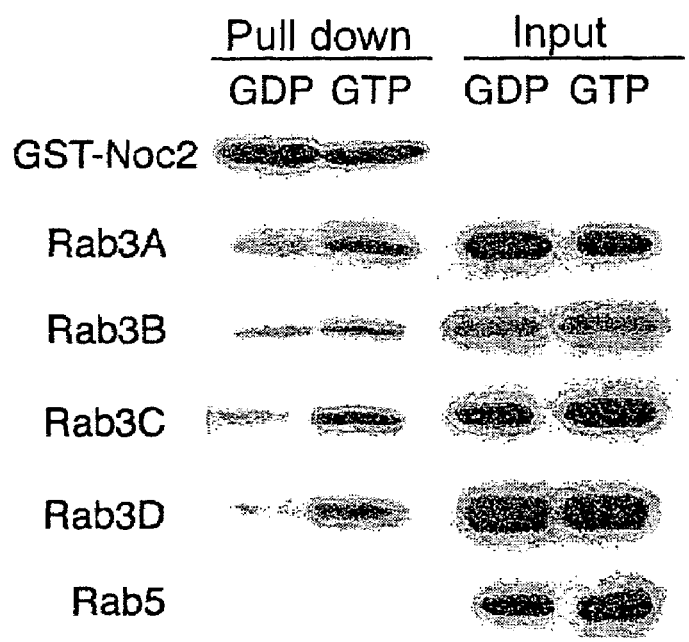
FIG. 10 shows binding of mouse Noc2 to Rab3 isoforms.
Figure 11:
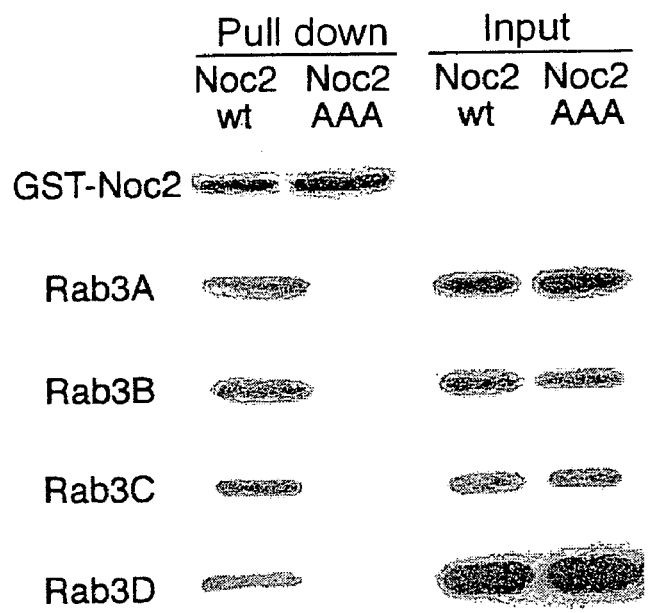
FIG. 11 shows binding of GST-Noc2 (wild-type, mutant) to Rab3 isoforms.
Figure 12:
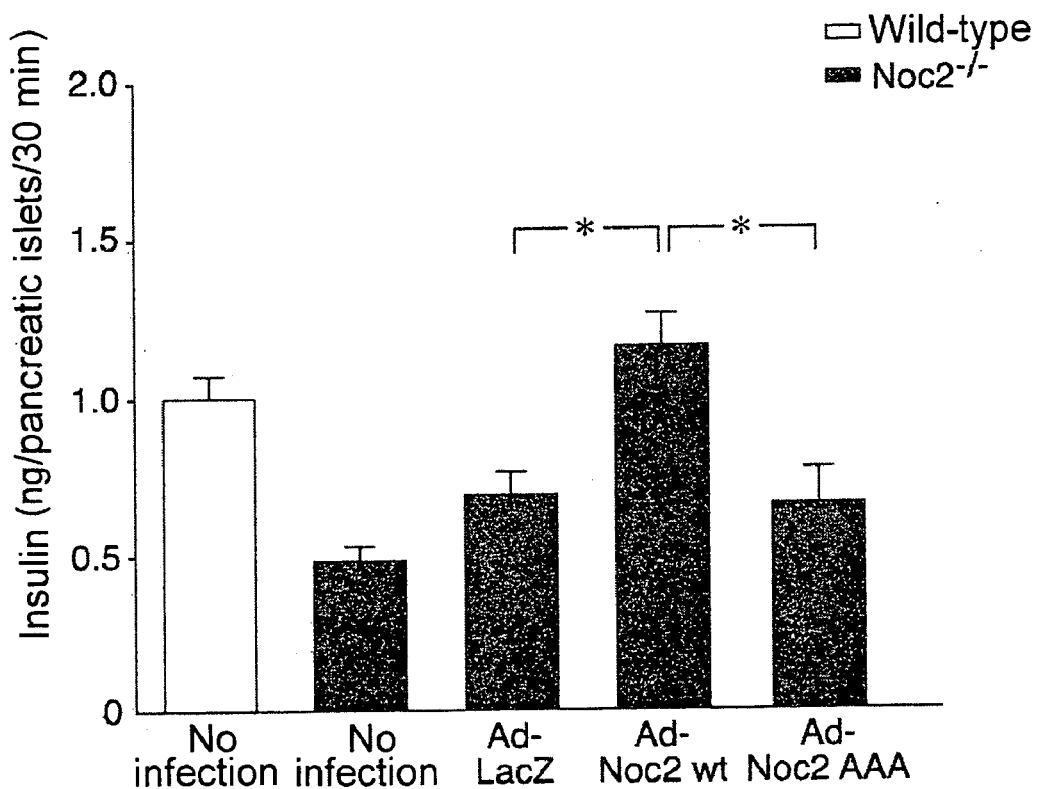
FIG. 12 is a graph showing insulin secretion from the pancreatic islets of knockout mice by being infected with a vector carrying the mouse Noc2 gene.

Noc2, which has high homology to the N-terminal region of rabphilin3 (16), has been shown to bind Rab3A (24). There are four isomers of Rab3 (Rab3A–D), all of which have been associated with regulated exocytosis (9–12). We found that Noc2 binds to all of the isoforms of Rab3 in a GTP-dependent manner but not to Rab5A (FIG. 10), indicating that Noc2 binds specifically to members of the Rab3 family. To determine if the effect of Noc2 in exocytosis requires Rab3, we generated adenovirus vectors carrying wild-type Noc2 and a mutant Noc2 (Noc2AAA)(24) that does not bind any isoform of Rab3 (FIG. 11), and infected pancreatic islets with there vectors. The defective $Ca^{2+}$-triggered insulin secretion in cultured pancreatic islets of $Noc2^{-/-}$ mice was completely restored by introduction of the wild-type Noc2 gene, while the mutant Noc2 had no effect (FIG. 12). That is, the defective $Ca^{2+}$-triggered insulin secretion in $Noc2^{-/-}$ mice was completely restored by the introduction of the wild-type Noc2 gene (0.69±0.07 ng/islet/ 30 min for Ad-LacZ, 1.20±0.11 ng/islet/30 min for Ad-Noc2 wt, n=9, *p<0.01), but the mutant Noc2 had no effect (0.65±0.11 ng/islet/30 min for Ad-Noc2AAA, n=9: Ad-LacZ, Ad-Noc2 wt, and Ad-Noc2AAA indicate the adenoviruses carrying LacZ, Noc2 wt and Noc2AAA, respectively)(open column; wild-type mice, filled column; $Noc2^{-/-}$ mice: values are means±s.e.m.). This indicates that the effect of Noc2 on $Ca^{2+}$-triggered insulin secretion requires interaction with Rab3. $Rab3A^{-/-}$ mice also have been shown to have a defect in insulin secretion (33). This complements the present findings and further suggests the necessity of interaction between Noc2 and Rab3 in the maintenance of normal insulin secretion. Though the trimeric G-protein signal that couples to Rab3-mediated exocytosis has not been identified, our present results show that Gi/o signaling is closely associated with Noc2/Rab3 interaction in pancreatic β cells.

Figure 13:
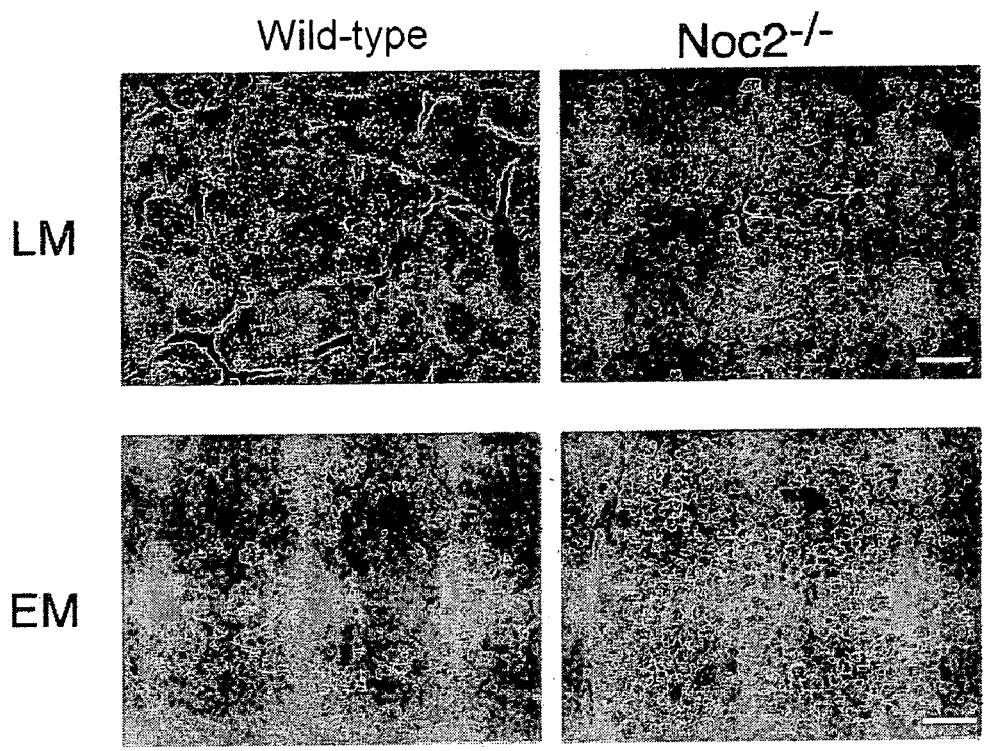
FIG. 13 shows light microscopic and electron microscopic images of mouse pancreatic islets.

We then performed morphological analysis of the pancreatic islets of $Noc2^{-/-}$ mice. FIG. 13 shows the results of light microscopic (LM) analysis of acinar cells of exocrine pancreas stained with hematoxylin and eosin (upper panel), and electron microscopic (EM) analysis of acinar cells (lower panel)(scale bar representing 10 μm in the upper panel, and 3 μm in the lower panel). No apparent abnormalities were observed in morphology of the pancreatic islets or the insulin secretory granules of $Noc2^{-/-}$ mice by immunohistochemistry for pancreatic hormones or electron microscopic analysis.

Figure 14:
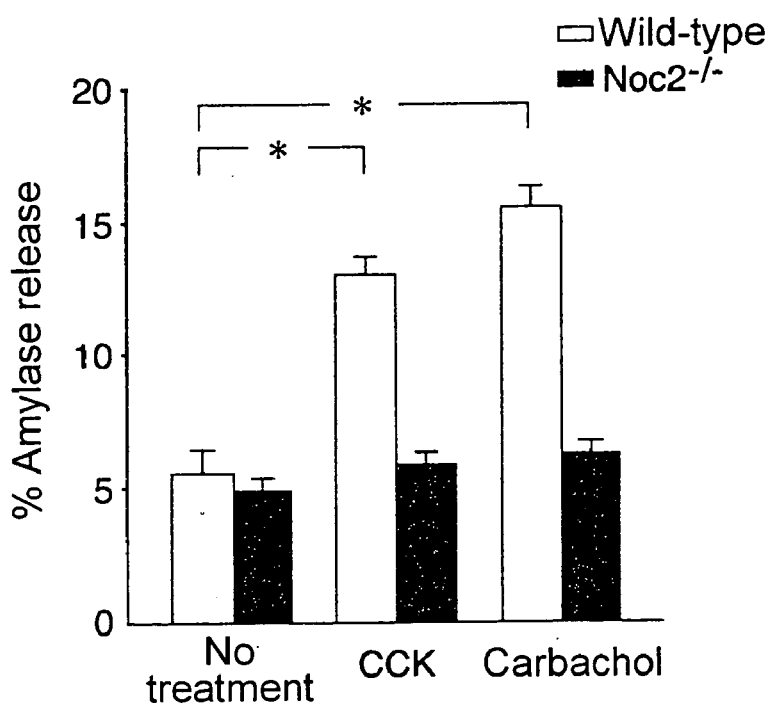
FIG. 14 is a graph showing amylase secretion from isolated mouse pancreatic acini.

Interestingly, however, a striking abnormality appeared in exocrine pancreas (FIG. 13, lower panel). Light and electron microscopic analyses show that the acinar cells in exocrine pancreas of $Noc2^{-/-}$ mice are enlarged due to a remarkable accumulation of secretory granules (zymogen granules) throughout the cytoplasm. To evaluate exocrine pancreatic function, in vitro secretion of amylase, a major secretory protein in zymogen granules (6), was examined (FIG. 14: open columns; wild-type mice, filled columns; Noc2$^{-/-}$ mice). In contrast to wild-type mice, there is no amylase secretion (% amylase released of total amylase content) from pancreatic acinar cells of Noc2$^{-/-}$ mice in response to either cholecystokinin or carbachol, both of which are known to be potent stimuli of amylase secretion [wild-type mice: 5.6±0.9% (basal level), 13.0±0.7% (CCK-stimulated amylase secretion), and 15.6±0.8% (carbachol-stimulated amylase secretion), n=12, for each, *p<0.0001, respectively; Noc2$^{-/-}$ mice: 4.9±0.5% (basal level) 5.8±0.5% (CCK-stimulated amylase secretion), and 6.2±0.5% (carbachol-stimulated amylase secretion), n=12: values are means±s.e.m.]. These results demonstrate that Noc2 is an essential molecule for regulated exocytosis of zymogen granules in exocrine pancreas.

Figure 15:
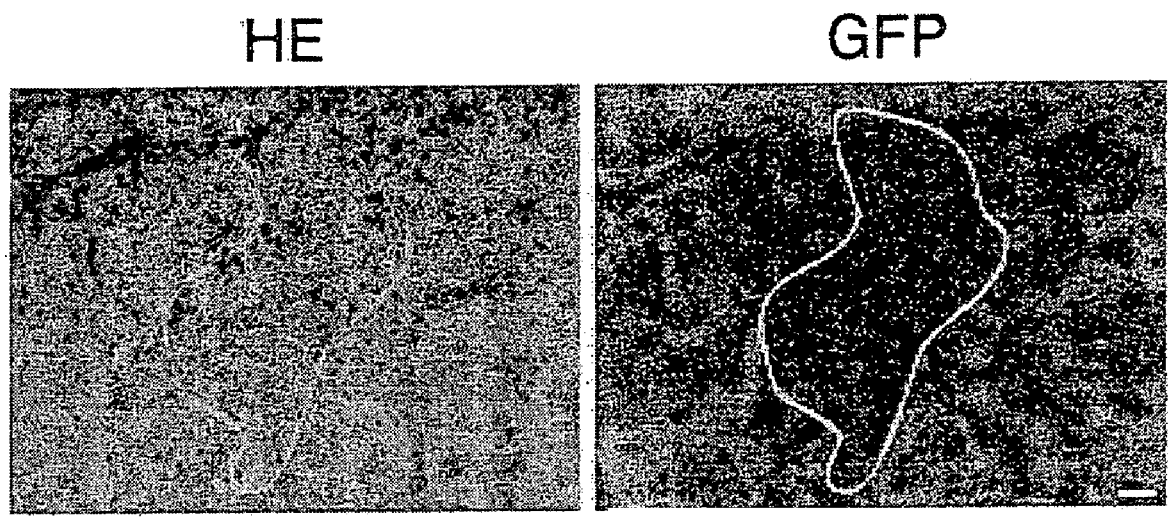
FIG. 15 shows hematoxylin and eosin staining and GFP fluorescence images of pancreatic acini from chimeric mice.

The acinar cells of Noc2$^{-/-}$ mice resemble those of mice lacking transcription factor NeuroD (NeuroD$^{-/-}$, mice)(34). In NeuroD$^{-/-}$ mice, the overabundance of zymogen granules in acinar cells is thought to be secondary to developmental defect in CCK-secreting intestinal cells. To determine whether the overabundance of zymogen granules in pancreatic acinar cells of Noc2$^{-/-}$ mice is due to a primary defect in the acinar cell or to a secondary defect in the CCK-secreting intestinal cells, we generated chimeric mice between Noc2$^{-/-}$ mice and wild-type (Noc2$^{+/+}$) mice which expressed green fluorescence protein (GFP)(GFP-Tg), by aggregating their 4 cell-stage fertilized eggs. If disruption of Noc2 in pancreatic acinar cells is directly responsible for the morphological abnormality, exocrine pancreas of the chimeric mice should show a mosaic pattern of mixed populations of both GFP-positive acinar cells with normal appearance (originating from GFP-Tg mice) and GFP-negative acinar cells with an overabundance of zymogen granules (originating from Noc2$^{-/-}$ mice). Histological analysis of the chimeric mice shows a mosaic pattern (FIG. 15). In FIG. 15, the left panel shows a section stained with hematoxylin and eosin (HE) and the right panel shows a section viewed under a fluorescent microscope (scale bar represents 10 μm). As seen in the figure, the exocrine pancreas of the chimeric mice shows a mosaic pattern of mixed populations of GFP-positive acinar cells (originating from GFP-Tg mice) of normal appearance and GFP-negative acinar cells (originating from Noc2$^{-/-}$ mice: circled by a white line) having an overabundance of zymogen granules. This indicates that the overabundance of zymogen granules in the acinar cells of Noc2$^{-/-}$ mice is due primary to the lack of Noc2.

Rab3D has been shown to be expressed in pancreatic acinar cells (35). Overexpression of wild-type Rab3D and its dominant negative form in pancreatic acinar cells has suggested that Rab3D regulates terminal steps of exocytosis of zymogen granules (12, 28). A study of Rab3D knockout mice has shown that Rab3D is not essential for exocytosis of zymogen granules but for the maintenance of granule maturation (36). However, the possibility cannot be ruled out that other Rab3 isoforms compensate for the Rab3D-deficient state. We previously reported that, as assessed by short exposure (36 hours) in autoradiography, Noc2 mRNA is expressed predominantly in endocrine tissues, but we also found, as assessed by longer exposure (1 week), low level expression in many tissues. We therefore examined histological changes in other exocrine tissues of Noc2$^{-/-}$ mice in which Rab3D is expressed (35), including salivary glands, in which acinar cells secrete amylase and various growth factors, gastric glands, in which chief cells secrete pepsinogen, and small intestinal glands, in which Paneth cells secrete anti-bacterial lysozymes.

Figure 16:
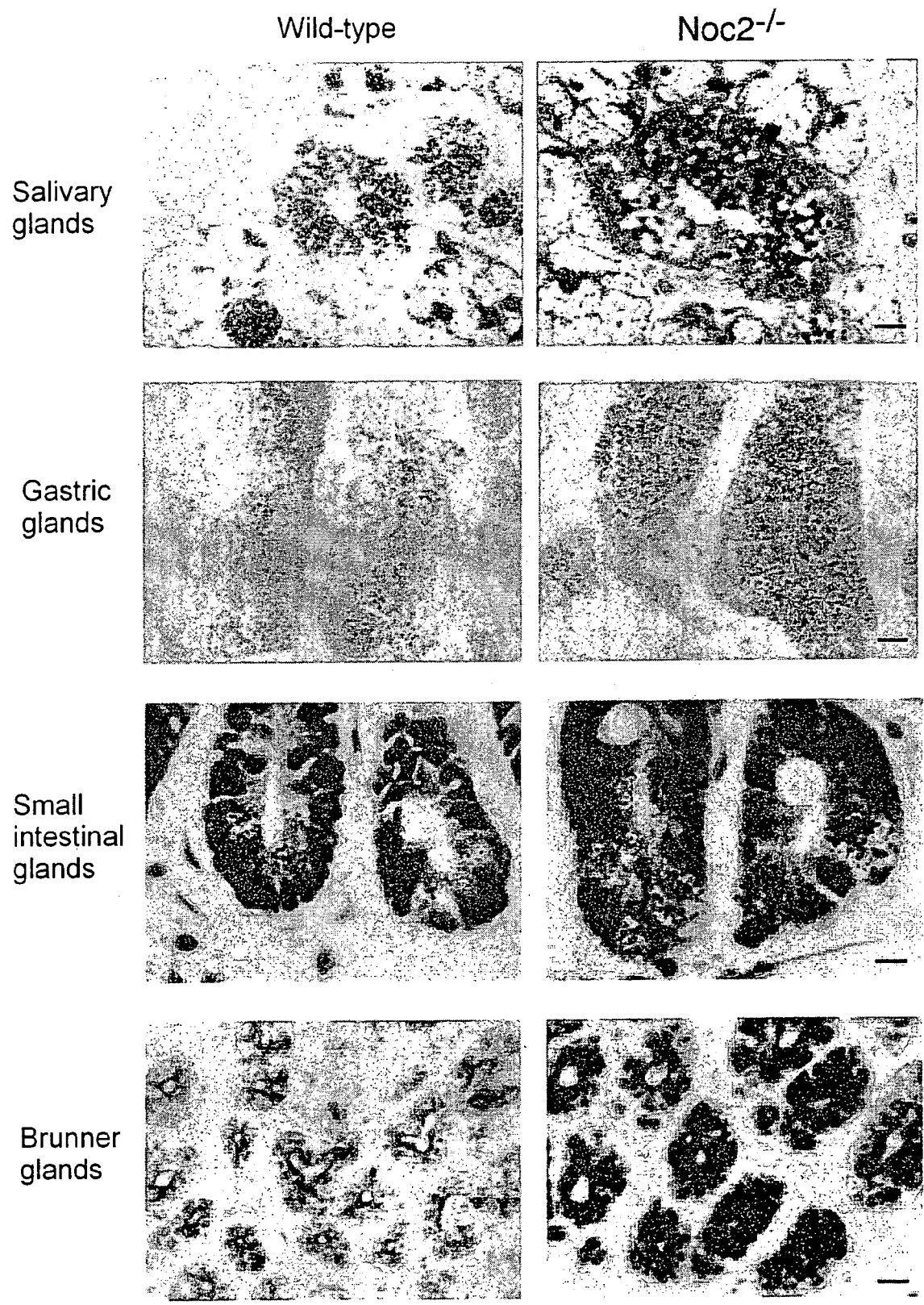
FIG. 16 shows electron microscopic images of secretory granules in exocrine cells of wild-type and Noc2 knockout mice.

An accumulation of secretory granules of increased size and irregular shape is remarkable in all exocrine cells examined in Noc2$^{-/-}$ mice (FIG. 16: scale bar represents 10 μm). In contrast, there are no morphological changes in the secretory cells of Noc2$^{-/-}$ mice in which only constitutive exocytosis occurs, including surface mucous cells of stomach and goblet cells of duodenal epithelium (data not shown). These morphological data suggests that Noc2, interacting with Rab3D, is required in regulated exocytosis in exocrine cells.

Determination of physiological roles of Rab3 effectors is a critical step toward clarification of the mechanism of Rab3-mediated exocytosis. Overexpression or microinjection of N-terminal or C-terminal of rabphilin3 has been shown to inhibit Ca$^{2+}$-triggered exocytosis in different systems (20). However, a recent study of rabphilin3 knockout mice reports that no abnormalities of synaptic transmission are found in Rab3A$^{-/-}$ mice, suggesting that rabphilin3 is not required for Rab3A-mediated exocytosis in neurons (21).

Study of Rim1$^{-/-}$ mice suggest that Rim1, as a scaffolding protein, regulates neurotransmitter release by priming synaptic vesicles in mossy fibers (17–19). Disruption of Noc2 clearly causes distinct abnormalities in secretory function in both endocrine and exocrine pancreas. Although Rab3 has been shown to participate in a late stage of regulated exocytosis, no intracellular signal that couples to Rab3-mediated exocytosis has been identified. Our study described in the present specification demonstrates that Noc2, interacting with Rab3, inhibits the Gi/o signaling that would lead to suppression of Ca$^{2+}$-triggered insulin secretion from endocrine pancreas, and that Noc2 is required for amylase secretion from exocrine pancreas. Accordingly, Noc2 is a critical molecule in the maintenance of regulated exocytosis of secretory granules in both endocrine and exocrine cells.

INDUSTRIAL APPLICABILITY

The present invention described above and defined by the appended claims can be utilized as a model animal and a screening system for the investigation of the mechanisms causing diseases of endocrine and exocrine systems, in particular diseases involving insulin hyposecretion, and for the development of therapeutic drugs for such diseases.

REFERENCES

1. Jahn, R. & Sudhof, T. C. (1999) Annu Rev Biochem. 68, 863–911.
2. Rettig, J. & Neher, E. (2002) Science. 298, 781–785.
3. Burgoyne, R. D. & Morgan, A. (2003) Physiol Rev. 83, 581–632.
4. Burgoyne, R. D. & Morgan, A. (1998) Bioessays. 20, 328–335.
5. Lang, J. Eur J. Biochem. (1999) 259, 3–17.
6. Williams, J. A. (2001) Annu Rev Physiol. 63, 77–97.
7. Takai, Y., Sasaki, T., & Matozaki, T. (2001) Physiol Rev. 81, 153–208.
8. Zerial, M. & McBride, H. (2001) Nat Rev Mol Cell Biol. 2, 107–117.

9. Castillo, P. E., Janz, R., Sudhof, T. C., Tzounopoulos, T., Malenka, R. C., & Nicoll, R. A. Nature. (1997) 388, 590–593.
10. Lledo, P. M., Vernier, P., Vincent, J. D., Mason, W. T., & Zorec, R. Nature. (1993) 364, 540–544.
11. Fischer, von Mollard G., Stahl, B., Khokhlatchev, A., Sudhof, T. C. & Jahn, R. J Biol. Chem. (1994) 269, 10971–10974.
12. Chen, X., Edwards, J. A., Logsdon, C. D., Ernst, S. A., & Williams, J. A. J Biol. Chem. (2002) 277, 18002–18009.
13. Shirataki, H., Kaibuchi, K., Sakoda, T., Kishida, S., Yamaguchi, T., Wada, K., Miyazaki, M., & Takai, Y. (1993) Mol Cell Biol. 13, 2061–2068.
14. Wang, Y., Okamoto, M., Schmitz, F., Hofmann, K., & Sudhof, T. C. (1997) Nature. 388, 593–598.
15. Ozaki, N., Shibasaki, T., Kashima, Y., Miki, T., Takahashi, K., Ueno, H., Sunaga, Y., Yano, H., Matsuura, Y., Iwanaga, T., Takai, Y., & Seino, S. (2000) Nat Cell Biol. 2, 805–811.
16. Kotake, K., Ozaki, N., Mizuta, M., Sekiya, S., Inagaki, N., & Seino, S. (1997) J Biol Chem. 272, 29407–29410.
17. Schoch, S., Castillo, P. E., Jo, T., Mukherjee, K., Geppert, M., Wang, Y., Schmitz, F., Malenka, R. C., & Sudhof, T. C. (2002) Nature. 415, 321–326.
18. Castillo, P. E., Schoch, S., Schmitz, F., Sudhof, T. C., & Malenka, R. C. (2002) Nature. 415, 327–330.
19. Koushika, SP., Richmond, J. E., Hadwiger, G., Weimer, R. M., Jorgensen, E. M., & Nonet, M. L. (2001) Nat Neurosci. 4, 997–1005.
20. Burns, M. E., Sasaki, T., Takai, Y., & Augustine, G. J. (1998) J Gen Physiol. 111, 243–255.
21. Schluter, O. M. Schnell, E., Verhage, M., Tzonopoulos, T., Nicoll, R. A., Janz, R., Malenka, R. C., Geppert, M., & Sudhof, T. C. (1999) J. Neurosci. 19, 5834–5846.
22. Kashima, Y., Miki, T., Shibasaki, T., Ozaki, N., Miyazaki, M., Yano, H., & Seino, S. (2001) J Biol. Chem. 276, 46046–53.
23. Fujimoto, K., Shibasaki, T., Yokoi, N., Kashima, Y., Matsumoto, M., Sasaki, T., Tajima, N., Iwanaga, T., & Seino, S. (2002) J. Biol. Chem. 277, 50497–50502.
24. Haynes, L. P., Evans, G. J., Morgan, A., & Burgoyne, R. D. (2001) J Biol. Chem. 276, 9726–9732.
25. De Boer, S. F., Koopmans, S. J., Slangen, J. L., & Van der Gugten, J. (1990) Physiol Behav. 47, 1117–1124.
26. Okabe, M., Ikawa, M., Kominami, K., Nakanishi, T., & Nishimune, Y. (1997) FEBS Lett. 407, 313–319.
27. Miki, T., Nagashima, K., Tashiro, F., Kotake, K., Yoshitomi, H., Tamamoto, A., Gonoi, T., Iwanaga, T., Miyazaki, J., & Seino, S. (1998) Proc Natl Acad Sci USA. 95, 10402–10406.
28. Ohnishi, H., Samuelson, LC., Yule, DI., Ernst, S. A., & Williams, J. A. (1997) J Clin Invest. 100, 3044–3052.
29. Carrasco, G. A. & Van de Kar, L. D. (2003) Eur J. Pharmacol. 463, 235–272.
30. Lang, J., Nishimoto, I., Okamoto, T., Regazzi, R., Kiraly, C., Weller, U., & Wollheim, C. B. (1995) EMBO J. 14, 3635–3644.
31. Renstrom, E., Ding, W. G., Bokvist, K., & Rorsman, P. (1996) Neuron. 17, 513–522.
32. Sharp, G. W. (1996) Am J. Physiol. 271, 1781–1799.
33. Yaekura, K., Julyan, R., Wicksteed, B. L., Hays, L. B., Alarcon, C., Sommers, S, Poitout, V., Baskin, D. G., Wang, Y., Philipson, L. H. et al. (2003) J Biol. Chem. 278, 9715–9721.
34. Naya, F. J., Huang, H. P., Qiu, Y., Mutoh, H., DeMayo, F. J., Leiter, A. B., & Tsai, M. J. (1997) Genes Dev. 11, 2323–2334.
35. Ohnishi, H., Ernst, S. A., Wys, N., McNiven, M., & Williams, J. A. (1996) Am J. Physiol. 271, G531–538.
36. Riedel, D., Antonin, W., Fernandez-Chacon, R., Alvarez de Toledo, G., Jo, T., Geppert, M., Valentijn, J. A., Valentijn, K., Jamieson, J. D., Sudhof, T. C. et al. (2002) Mol Cell Biol. 22, 6487–6497.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever.

In the foregoing and in the following examples, all temperatures are set forth uncorrected in degrees Celsius and, all parts and percentages are by weight, unless otherwise indicated.

The entire disclosures of all applications, patents and publications, cited herein and of corresponding Japanese application No. P2004-110374, filed Apr. 2, 2004 are incorporated by reference herein.

The preceding examples can be repeated with similar success by substituting the generically or specifically described reactants and/or operating conditions of this invention for those used in the preceding examples.

From the foregoing description, one skilled in the art can easily ascertain the essential characteristics of this invention and, without departing from the spirit and scope thereof, can make various changes and modifications of the invention to adapt it to various usages and conditions.

What is claimed is:

1. A transgenic mouse whose genome comprises a homozygous disruption of a Noc2 gene, the homozygous mouse exhibiting, in response to water immersion stress, higher blood glucose levels with reduced insulin production together with lowered response of insulin secretion after a glucose load, and further exhibiting abnormal acinar cells of exocrine pancreas due to accumulation of secretory granules.

2. A transgenic mouse whose genome comprises a heterozygous disruption of a Noc2 gene, wherein the mouse, by crossing with another said mouse produces a mouse whose genome comprises a homozygous disruption of a Noc2 gene, the homozygous mouse exhibiting, in response to water immersion stress, higher blood glucose levels with reduced insulin production together with lowered response of insulin secretion after a glucose load, and further exhibiting abnormal acinar cells of exocrine pancreas due to accumulation of secretory granules.

3. A tissue of the mouse of claim 1.

4. The tissue of claim 3, wherein the tissue is an endocrine tissue or an exocrine tissue.

5. The tissue of claim 4, wherein the endocrine tissue is selected from the group consisting of pancreatic islets and pituitary glands and the exocrine tissue is selected from the group consisting of exocrine pancreas, gastric glands, small intestinal glands, Brunner's glands, salivary glands, mammary glands and acini thereof.

6. A cell of the mouse of claim 1, wherein the genome of said cell comprises a homozygous disruption of a Noc2 gene.

7. The cell of claim 6, wherein the cell is a somatic cell or a germ cell.

8. The cell of claim 6, wherein the cell is selected from the group consisting of a pancreatic β-cell, an acinar cell including a pancreatic acinar cell, a fertilized egg and a germ cell including spermatozoa and ova.

9. A transgenic mouse whose genome comprises a homozygous disruption of a Noc2 gene, wherein disruption of the Noc2 gene comprises removal of exon 3 of the Noc2 gene, the homozygous mouse exhibiting, in response to water immersion stress, higher blood glucose levels with reduced insulin production together with lowered response of insulin secretion after a glucose load, and further exhibiting abnormal acinar cells of exocrine pancreas due to accumulation of secretory granules.

10. A transgenic mouse whose genome comprises a heterozygous disruption of a Noc2 gene, wherein disruption of the Noc2 gene comprises removal of exon 3 of the Noc2 gene and wherein the mouse, by crossing with another said mouse produces a mouse whose genome comprises a homozygous disruption of a Noc2 gene, the homozygous mouse exhibiting, in response to water immersion stress, higher blood glucose levels with reduced insulin production together with lowered response of insulin secretion after a glucose load, and further exhibiting abnormal acinar cells of exocrine pancreas due to accumulation of secretory granules.

* * * * *

SEQUENCE LISTING

<160> NUMBER OF SEQ ID NOS: 8

<210> SEQ ID NO 1
<211> LENGTH: 1934
<212> TYPE: DNA
<213> ORGANISM: Rattus sp.

<400> SEQUENCE: 1
cgaagcagat gtgactcctg ccctgggctg tgctccccat catggctgac accatcttca    60

| | |
|---|---|
| gcagtggaaa tgatcagtgg gtgtgcccca acgatcggca gcttgctctg agagccaagc | 120 |
| tgcagacagg ctggtctgtg cacacatacc agacggagaa gcagaggagg actcaatgcc | 180 |
| tgagccctgg agaggtggag gtcatccttc aggtcatcca gagagcagag cggctggaca | 240 |
| tcctggagca gcagaggatt gggcggctgg tggagcggct ggagacgatg cagaagaacg | 300 |
| tgatgggcaa tggtgtctcc cagtgtctgc tctgcgggga gatgttggga ttcctgggca | 360 |
| gctcctctgt attctgcaaa gactgccgga agaaagtctg caccaagtgt gggatcgagg | 420 |
| cttcccccgg ccagaagcgg ccctgtggc tgtgtaagat ctgcagtgag cagagagagg | 480 |
| tctggaagag gtcaggggcc tggttctaca agggctccc caagtacatc ttgccctga | 540 |
| aaaccctgg ccgggctgat gatccccact ccgacctct gcctgtggag cccacagaac | 600 |
| cacagcctca gagtgctgaa gtcagccgtg tctacacatg ggcccgaggg agagtggttt | 660 |
| ctagtgacag tgacagtgac tcagatctca gctcctccag cctggaggac agacctatgc | 720 |
| cctctgggat caagggcaca aaatatgaca agcctagagg ggactcaggt ggcagcatgg | 780 |
| agtcacccag gatggggcct gcccgaccgc ccagccatct ttctggcagc cagagcagcc | 840 |
| tgggcagtga cagggggca ggtgctcag atccacaggg aggcaccta ccccggcctg | 900 |
| agcccagggt atccggcaaa aggcatacct gggcaactac ccattactga ggtggccggc | 960 |
| tgacctccct gggctgaggc acactctctg gaggaagatt cagagagaga caacagggcc | 1020 |
| ggcctaccgg agccctctc tgaaggttct tgagggctca caagctccct gataccttga | 1080 |
| cctgcaactc aacaagccag tgtttgggga ccgagcgtgc ttgccccac cctgtagtgc | 1140 |
| cttctctact atctcactca gcaccccacc ttttatttat tgcccctccc ccatcccagt | 1200 |
| cacatctcga tttgctcggg ccttggggtg ggttggaaag gccttcctct atgcactgaa | 1260 |
| gtttgggtgg gacacacagg gctttctttg tactaatgat gcgcactcta accctcagtg | 1320 |
| tgaccctgcg gagctgagca accccacccc acaccccac accccccac cccaccaca | 1380 |
| ttcccagtgt aagcctggag caccaggctg tccctattcc tccaaccggc gggcggcggg | 1440 |
| gcggcggcgg aggccagagc aaggtcctat ttgccccgag gctggtccag gagctgagtt | 1500 |
| aaatccagct ttgaggtttc cccgaagccc ctattggcct ctgggttttt gttctaccct | 1560 |
| gaaacacagc tcccctcag acattaaaat gcttttttgtt cttcagtgga aaacaaagct | 1620 |
| cccaccctgc ctcatgctcg ctggcccagc ctgggagttt caaattctaa agccagagca | 1680 |
| agcgtgaaaa atattcaaaa tacagatgct tctggaaaac ccctccctgg ggtgggggtg | 1740 |
| aggaagtgtc ctatgcccctt ccttccctga gtccagttcc atccttcccc accaccatcc | 1800 |
| ctcccattat tattattaat aatggccacc accattatta gccttttgcc tgttgctgct | 1860 |
| ggcagaagac aaacttcact atttccctga gatgtgtagc catcagcact aacataataa | 1920 |
| acataagaat tttc | 1934 |

```
<210> SEQ ID NO 2
<211> LENGTH: 20492
<212> TYPE: DNA
<213> ORGANISM: Mus musculus

<400> SEQUENCE: 2
```

| | |
|---|---|
| attatggaac caggtgctag gacacttctc aggctcacac aggtcagtaa gtgaaggta | 60 |
| aagcttccct ccccatcttg cccctcacct gagttctagt gcctgcatat taagaaggat | 120 |
| gcttctaggc tctgaaactt gttcttaggg agtcagggag cacaagtgga tagagccatc | 180 |
| attccttgaa ggtaaacttc ccagacaaaa aagctggcca caacagaatg tgatcttaat | 240 |

| | |
|---|---|
| caggtctccc acagataatc tctcaccaag agcctctccc cgcccttata tctcactgca | 300 |
| ggtattggga ttacaaatgc ggtctactgc acctggcttt tatcgtgggt cctgtggagc | 360 |
| tggtctcaga ttgtcagact tgcatgaaag gcttttacat gccgagccac cactgcagcc | 420 |
| caagatcagg catggtggga cacccaggct taatcccagc acagcataga gggtttgaag | 480 |
| caacaatact gtaataagga aaaggaaat gagaggaaaa agttttcata tgctaaaaag | 540 |
| gctggtaatg tgtaagacag ctagggaatg gtctggtcaa caaaaagacc aaggtatgct | 600 |
| tagacgattc actccttaac cccagagagg agagagtcgg gagtcatggc caacagtgta | 660 |
| accagtcatg ttagcctcca ttagaacccg caggataggg tccaggacag tgaaggaggt | 720 |
| ctatacacag aggcttccac ccaccccacc ctaaccccac acacctttcc atctgactgt | 780 |
| cctttctaac aaaccaggag ggcgtctccc tgaactgtgt gagccatctc cacaagccag | 840 |
| tctagtccaa gagagccaca tggctggtgg cctggtgctc cacagctgag cttctcacca | 900 |
| gcaccgacct gaagtgagct tgtgcaact gagcccttac ctgcaggacc tgactggtgg | 960 |
| agatctctca accagaggat ctgctgccca gctgatccct gcacatttta gggatcaccc | 1020 |
| ttgcttgttt ttctcctcgt tttagggcct gatcctcaga acaggacac caagcttgct | 1080 |
| tttggcggct tcatagtctt cgtgtgaggg tggaatagga gcctgtgcta actctcgcca | 1140 |
| tctatacccg gaatttggat aatggtatca gttgagctca gggacaatga cattgaagct | 1200 |
| ccagattaaa cagaagggac acaataaggt ccattggctg ctggggagag agacagtaga | 1260 |
| cttctagaca tgtagacagg ggactgggag aaggagagag actcttcctg tttggtcctg | 1320 |
| cttttctctcc ccagccttgt ctctctctca gctcaccaag cccgtcacac tagcctcatg | 1380 |
| gtttatcatc tactcccatc tctgtggaga ctctcctgtc tccaagggtt ttgtccaggc | 1440 |
| tgagcctcat gcctggcaaa catcttcaca cccttatggc acatccgaaa atctcctcct | 1500 |
| cccttgctcc ttccttgagc tcctccaaga gacactaatg tcttccctgg tccccttttca | 1560 |
| ggtgtgaggc catctccaaa gcagtgctga ccacatcaca ctggatagtc tccttcctga | 1620 |
| ccagctcccc tgagtcaaac ccaaggctct gcaggtgcta ggcaagtact ctattcctga | 1680 |
| accatgctcc tgactcacat tgttcatagt tgattcccag tgctcagcaa gagcctggaa | 1740 |
| cagagttgtc tgtcacagga ggggaggtta agtgctaagc acagatgcca caggtgagct | 1800 |
| ccctctgtgc ctggagcctc aggtggccta tggagcattt aaggagggga gagatgtgac | 1860 |
| tgcagagact cactcattct tccagctctg taatctggcc tctgtattct tagaacttct | 1920 |
| ttctccagaa cattctcagg gtatgttgat ggtatagtgg tgaatatctt ctgaaacatt | 1980 |
| tccagaaact tgcagaattc ctggatctcg gtgggtttag aaggcaggaa ggcaaaggcg | 2040 |
| gctcattcag aggcctgacc agcagtttgg agggaggaag gaggagatag ggtataggct | 2100 |
| tcggtatttc agtctttgtt cctacaatcc cttggaagga ggactgttca tcacagttac | 2160 |
| atagggaagg tctggaagaa agatcagggc agcagacact agggcaaggg atgatacaca | 2220 |
| gactcggggg tggctgtggg aaggccttga gctcagcatc cttttaatat tggggagtaa | 2280 |
| tattgtactg ttgattaaac atgtgggagg caccaggctt tgcccttatt cacagagccc | 2340 |
| ataagtactt atgtgaagga aagaaaacag taagagccga ttaatggcag acccggggga | 2400 |
| ggtagcaccc tgaggctcag gaagaagtgg cagaaaggct tggtggcagg gcctggtaca | 2460 |
| ggtgagatgg gagaaggcac agctcagagg ctcactgggc accagcaatc agctgatcag | 2520 |
| gaagggcct tgagtgggga ggtctcagac ccaaggaaac agtgatgtaa taggtaggat | 2580 |

```
ggacaagatg acagaatgga caacgtacaa agaggaagga ccactatcct tgggcccagg    2640
gcacagtcag gcagccagag gctgctgggc ctgagaggct ggaccatagg cagcaaaatg    2700
agggtctgg  aggcttggtg tagctatggg tcaaagtggc cagtccacag cacccccaaa    2760
aacaccagtc cacacagacc cctagccaaa gtcagtaggt tgccccagc  cccccccccc    2820
agattgcccc ccccaagctt ggcacctgta ctttgtcagc tctaccttgt tctagaagaa    2880
catcaagggt ccctctggcc tccaaggatt acattagccc catcccctc  tttccagcga    2940
ttcagacaca accagtaggt tccttttga  actgttttgt tttcatttgg aaaaaaaaa     3000
aaaaatccag cagaccagac aaacatccca gagcttctaa cagtctgggt aatgtgctaa    3060
tggctaatta gggaccctgg tgatggcagg cctgaagctc tgtgggaaac aatgacaaga    3120
cagggtcagg tggagacaga cccactgggt ggagttagtg ccaattatgc tagaaagtca    3180
acaagcagct cccactgccc cacagaagg  aggcagaggc cctggcacca tgtagaggat    3240
tttagacttt gttctacata cagtaggag  tcacggaagg cttcagggag actcagagaa    3300
tggtgtgagc agagcaagat gtaagagggc aggagcagag actgagccgg gaagtagagc    3360
cagacagctc ggccctttcc ctgcacccag ggcgtgggg  ctcataccct ataggaccaa    3420
cttcactcct gcctacatgg tggtggtggt gttcgagtca ggatttctct gtgcagccct    3480
ggctgcccca caactggctc tgttctctgc tcgcctcaaa ctcagaggtt cacctgcctc    3540
tgccttcgag tactacccag ctcttgcctg cgtctgaaca tggtttctaa gaaggcatgt    3600
ctctctcctt ggaggtagat aaaaaaggag aaacaaattt caacggaatg gggctagaga    3660
ccctccccct ccaccaaagc atctaataaa gccacaatta tttatttta  ggggattat     3720
ggatggaacc tcttataatt taggaaagta atctaccatt aagtccctag cccttggtcc    3780
tttgatgctg gaatttccag ctataccatt ccgaatgcac ctgaccttgt ctgattctga    3840
ggttggaggt actgggagcc tgaggaagaa gagccagttc tccctcccc  cacccgaccc    3900
ttgctctctg ctctccatca gcagagctgt cctgatgccc ccaggatgga gaaggactga    3960
ctacccacac cctgagctgt ggtcagtgag caactgacag ccctggggaa aactctccag    4020
caataaagag gcgatgtgag agcaaggaag agtcgcaggc ctgctgaagt gtggcagctg    4080
gcagggcagc cggagagggg taccacgtgt cgctgagcca caccgtggac tggaaatgtc    4140
attatctgct atttaccacc gcagaggaca agtgagtcca caggattacc tctgctaaga    4200
gcgagccact aaacagattg cccagcggca cttcctgctg ccggagcctg cacagctct     4260
acccaccaga ccaggaggaa ggagctgcaa ctgcagtagc cagggaccct agggggaaggt   4320
gggtggtggg cacacatggt taaggcaggg aagtgtgtca ctgtgaccca gcctgggcaa    4380
gtccacggag cctgggcagg tttgcttccc acccttggga gataggagct cttagtcact    4440
caattaggca attagcctca gggagactca aaccagaccc ctacaaactc cccatgtccg    4500
tccagacgtc tccagatcat gacaaaccag gccagactgt gacaactgcc tcagggagcc    4560
aatgctagcg gccgctcccg attctgtaac ctgccatggg cgtggagttg cttctggcat    4620
tggggcaccc catctataag gtgacatctg gtctcctcc  ttttagggga ggtctcctga    4680
atattttcag ctctcttcct ttatcataag gtatggagat aacatctcaa ctaggctgag    4740
ctaccacaag tgagctgtat ctccaagctt ctatttctcc ttctagaaaa tagtctaaac    4800
acattgcttt ttgactatca cctaacagtg gtgggctgtg ggaactcagg acagtggaac    4860
tctcagagca caccaaccca tgtgggcctc tccctgaccc aaggcacaca ttcctgagct    4920
caagagggct agaaagcaaa ctagagtggc tttaaagcct cctcaagaag agcctggtgg    4980
```

```
tggtggcaca cacctttaat cccagccctc aggaggcaga ggcaggcaga tctctgagtt    5040
caaggccagc ctggcataca tagagtttaa gaatggctag agaaaccata acttggaaaa    5100
acaaaaacag caacagcatc cacataaagc cccagaagaa cgctcaggca ggcacagagg    5160
ttacaacagg gaggctgctt cagctccttg ctgtacctgc ctcacactga cccccagtct    5220
gtgaatggaa actgggtgtg cctaagcaca caagatgaaa ccgcttggaa gagcctatga    5280
tactgtctag ttcaacccct tcctctcaca tgggcctcga ggggagtggg ggataaagtg    5340
tgtgtgtgga ggaggaggga ggaggggtga ttttttttcat tcaaggtcac atccatccat    5400
cggagggaca gggctgtgtg gccctattgt agtgggtata ggagggcaga taaggatggc    5460
cttagacaac aggattccca cccaacccac agaaagacca aggaaccttc tggaaataag    5520
cttgaactgt cacacctaga tttcagacac gggtaggcat ggttgtgggg tcagtgtgca    5580
gaggcaagtt gcaggggatc tcagaaggaa gacagactaa ggaacgggat gggagatgtc    5640
tgctgtctaa gggggtaggc atccattcac ctcactccag ctgtggcccc tgcaggctgt    5700
gagtaacctg gaagaaggc ctgcaggaa gtgtggaaat ccccttatat tatcacatag    5760
ttcctaaaaa cagaattgga ttgttttgcg tgcgtgtggg tgtgggatgt tgattctgat    5820
gtgatatgaa gtgaaaacat aaacaaaaga aactacagaa taagaaatat atttaggttc    5880
atcaagaaaa tacacagaca ttgccaggca ctgccataga ggtaggtgga ggcctgggag    5940
cccattgctt gggggacaag ggtggaaaga ctagaaaatc aagactatct cagctacaca    6000
gcaagtttca agccagccag ggttactttg caagaccctg tcttgagaac aaccttctcc    6060
cgatatatac cctcagtata caaataacat atacatctgt agacaacata taccctcagt    6120
acacaaacaa catatacatc tgtagacact tggatgtgag agaagagttt agaaggaaaa    6180
acacccaaac tcttagggtt agggctgggt aaatatttta cctacatttg tataaactaa    6240
ttctccagca gtcattgtgc acgagacacc acctctaaga gcgtatcaca tgcctaactc    6300
atttcaatcc tcacaaccac actccaaggc aggaaaactt tgattatctc caatttccag    6360
gtcaggaaaa tcgaggcagg agaacatagg caactgaatg cagtaatgga gaccacttgg    6420
cactagaatc tatcatcttt taaaagtcca agagatggcc aggaggcact tgcctagcat    6480
gcttgaggtc ctgtgcccac atcctgcata atacataaat ctagggagag acgagtctca    6540
aggttaagtc ttgctgggtc tttaagaccc aacctcggac ctcttgctta ctggttaatg    6600
gcataaccat gggagaagga ggtctccttc ctgttcacat ctgtggtact gggaatgaag    6660
ccagagcctc atgctggcca agctctccca ctaagccata tctctagccc ccttctgacc    6720
ctctggagcc atcaggtgct ttaggctaag aaagggaggg ccagaaagca agctgtgtcc    6780
ctgctcagtt ccaccaccat gatgccaggc ctgaaaggat gcaagctgtg gacatgccca    6840
agctctgata aaccattatg gatagtcaac ttgtaatccc tacaattttt acccattaga    6900
agcttctctt tgcatttgtt ttcagtcctt gttaaaaatt cactctagct catgggttgt    6960
tcaaagcagg ggagacccct gacctagctc ctggtggagg gaggactagg tctgccagcg    7020
tgctcatggc agactccaga gtaaccggca atagccaggg agggatcttg ggttttggaa    7080
ttggggttga agctggagta tacacactgc ggctggctgg ggctgaaagc tcgtcctggg    7140
gtaagatcct gcccttaggt cttagtggct gagcctgggg cagtctatgc tctgctgttg    7200
aagatggctc tggaatgctg aggagttagg cagggaagaa ggcttagctc atattctctt    7260
catattcctc ttatccttct gttcctcatg ccccactgga cagcattgtg gggtcacaag    7320
```

```
gtggttcctt agttttgtgc tactctcagc ctggatgacc tggccacaca caacaggcac    7380
ccagcatctg gtcctggctc actgacggca tagagaagcc gacactgaac agcaggatgg    7440
taggccatgc aaacatcacc cgacaggcca cgccctcacc tactcctttt gccctggtct    7500
tttcatagtt ctcatgttct gagacacagc ctgctggtaa ggccattaag actccacttg    7560
gggaaggact tcgtccnctg ctttgtatcc ctttcctcac ctgaaagtat ggctggccgg    7620
ttcccatggt ggctttggtg acaaagagga caagggccct ggcaatggag gcagctgtca    7680
attactagaa agcttttttaa aagtcggggt cttatatagc ccagactggc cttgagcttg    7740
ttgaagacgg ccttggggtg tgcaccacca ccccagagtt tatacgatgc tttgatcaaa    7800
cccagagctt caaaccactc aagaactcgc caatcgagcc atagcncccaa ccccaataa     7860
ctcaaacttg tttcattaat ttctcttcct tgtttctgaa taatatcctg gtttcccgcc    7920
taatctaggc cctggctact cttttcccttt gggacacaat ccagtctttg tagcccaggc    7980
tagccaggaa ctctgaatca tctttttttc agcctccaaa acggttggat gacaggtgtg    8040
tgccaccacc cctggtccct gctgcatggc cagttcaggt gtcggtgtat tcctgccaac    8100
ctaccacagt gccccaggt ctccctgaga catctgtgtg gactttgcct ctctcacaga     8160
tctcaggact gctcagctct cttgggtgac tctagtgatg cttcagcctg gctttgaagc    8220
cccttcttgt cttcctctct ccttagtctg ccttctccc ctcctcctc atctcagtct      8280
cccatatacc aagtgcttag cagccctgtg tctctgcaga gccacatctg ctctagccat    8340
gtcctgatgg gcacattttc atccctccaa cattgctctc catgaacaga ggctgcccag    8400
catccccat tgttatctgt ctgggggcct ctttcagctc tcctacagaa ctccttctcc      8460
tatgtacgtg taagcctggc atcccttggg agtcaggtgg gcacaatgtc cagagctgca    8520
gaactaacac gcaggccagg gatggagaat cagtccactg agctaagggc accactggcc    8580
aagagggcca tagcccacct tcttctatcc agatgacccc tatgaacagg atggactggc    8640
aactgcgtgg agtggcagtt tctttatttg ggggaagaaa ggctgtctgt gggctctagg    8700
cagcagggct cgtgtgcctt aatgnagatg ttctgcttgc caaccccagg cgaggtggat    8760
gttccaagat acagcttggt gtctggtcca atcctctgat cctaacaaca ggagccaagt    8820
caattcctgc caaacagcct tggtgacagg cgagctgcct gagcgggccc tcagggcag     8880
aggaattaag tgactctttc cgggaattta ggaaacatca gtagcagaac gaaaaaaaat    8940
ccatctttgt aataaggcac aaacacacgc cttccacatc aaattaggcc gaggaggaca    9000
aaggacacag cgaggccaat tcagaggcag ctaggataaa tatgctatca ctcaaggtgg    9060
ctggcggcta tctctatgct ttctctcccc tctccccag gagctgaggt gcttaagatc     9120
aggcttggaa agggaggtca ggatgggagc cattaaggac ttccggcata ttccaattcc    9180
ctgcccccc ccaaaaaaa agactttttc ctgacttttg cacattggtg gcggcaatgt      9240
aaaattattc agccctgtg cagaacagta tggcggctcc tcacaaagtc atgctgaact     9300
actgtgggat gcagctatgc cactgctggg catttactcc cagggattg gaagcgggat     9360
ctcagagaga tcagcacaac cacacatata gtcacgggtt ttacaagagc taaattgtgg    9420
gagcgctcgg ggtgtccatc acagatgagt ggaccagcag aagtatggtc aaagagtcac    9480
cttgaaatgt tagtcccttc ataaggaga ggatggcact tgaagacatc acgctaatga     9540
atctgatgaa atgcagactc tggctcagga ggttccaggg gggctgagaa tctgctcttc    9600
cagccagcac tgaaggacgt ctgtgcctct ggtcctccgt ctgtactttg cgtagctggc    9660
acttgagttc tttgactcct ctggtgtctc catctgcagg aggtggtctc tgaggactag    9720
```

-continued

```
ctggggagca ctcccagatc ctcacaagga gcacgtgaga tctctgttca gaatcagcag    9780
gctttctagg aagtgctgca gccagcggat cccaagctgg ggacaagtgt gagacagtga    9840
tggggaggga ctctcttccc tcagattgcc caggcgtggc aggcaggagg gtaacaagca    9900
agtgccatct gctcccccca ccccagccca ttgctcagca gccacaaatc cctcaccctg    9960
agcagaatgg agtctgctta gggttcaggg ggaaatgaca tagcctcttt ctagcctggg   10020
gttactgcca ctctctgcag caagaaacag atccttagag caaaatggtc tggagcccgt   10080
ggcaggagag atcagggatg gaccagcccc tgccctacag ttttctccaa tgctgggctg   10140
gggccataat gccccacag aacttttgct aagggcctgg agaaaactgt gggctaacct    10200
cagcccctct gcttctagga ctcagcacac aaggtctaag ttatgtcagg ctgcctctcc   10260
tgggcctgca ctatgagatc catttggttg agaccaggaa aagctccaac tgcttcctta   10320
gactggtgac agtgctgtcc tggggctcag atggtcatcc tgcaaccggg cacagcctcc   10380
catggctgcg aagctgctgg ctgacttgga tcggaggcaa ttagaagtac caggcctctt   10440
taattaacca gtcagctcct ctccctttc actactgcca gggaaacgag gccaggcagc    10500
cggagtgtgt gtgtgtgtat gcacgcgagac ccaattacag agggccacag ctccaggact  10560
gcagtgcctt ctacctgcat gttcattagc ttgtggctga cagacactgg cagggatctt   10620
gctggaggga cattggtgtc cccaggagca cctgaggatt tgtccaccac ccacacaggt   10680
ctggcttgga cccttccaat gccaagggtc ttcccagtat cctctctctg cagcctgttt   10740
aaacatacac cttctggtct tgggagactc gctcttccac acagctctcc gggttgctaa   10800
gtcctgggaa cctaggcccc tatagcagtg ggtgtcactc tagagaatgt tgcccatcca   10860
ccttgacagt caggacctaa gggaagaatt ccctctcttc tagattcccc tcaccctga   10920 aagacacaca gactgtgcct ggatgaacca ttggcacctg cacattcatg gggccctgcc   10980
agctcgacac caatattgag aaccgcaaag gtatccaagt ccttaattta gttacataac   11040
tcttggaaaa gaaagactga attatggtgg cagcttcaat atgaagctca agaaagcacc   11100
agtgcttcca ggcatggtgg tacccatctg caatcccggc attccagagg cagagacaga   11160
agcgctgaac tggaggctac aatgggctag ataggagact tcattttaaa gagatagaga   11220
cacacacaga gcatgtgtgt gtgtgtgtgt gtgtgtgtgt gagagagaga gagagagagg   11280
gcgagagaga gagagagaga gagggcggga gagagagaga gagacagaca gacagacaga   11340
cagacagagg gagagggaga gggagagaac ccaagaaaaa agcaaacaag aaaccataac   11400
atgaattcta ataaggaaaa tatggggtac aatacactaa attgggtctc tcaaaagctc   11460
agtgtgttga actccaagtc ccgttgtgac tatcttggga gaaagggtcg ttcgtctgca   11520
agtaaagagc tcaggttaaa tgggatccga agtgtgaggc catacctgat gtgattaatg   11580
tctgtaaagg aagaggcagc agggctcctg cctgatgccg tatgaggaaa agccatcca    11640 tgaggcaggc cagggagacg tcgacttgcc ttggacttcc cagtcacaaa ccacaggaa    11700 ataaataaag ggttgttagg gcatcttgcc ccggctggct gatctgtgcc tcgctctgtg   11760
tctcctgtga tcatgatggt cgggtccatg ctctgtggca aacctctgag cagggagccc   11820
ctggggtggc ccggtcacca tgacagtgac agggtgcccc tgcctttgct aggagctagt   11880
gatggagcag gctgtgaagg gcttccttgc atcagctaat ccatccctca catccacctg   11940
gtgctgatgc ctgcctttcg accttgtctt acagataaag gaatgaaggc ggagagaggc   12000
ggagtgagtt ttaccagagc cctccacaga agcaatatgg gaacgggacc caagccggtc   12060
```

-continued

```
ctacagctgt gggtacctct gtacctctgt tcctgcttcg aggaagagag aaacacccct  12120
caatttgtgt ccacaggcag gcaggcaggc aggagtcaca ggaacttccc agggctagtg  12180
tgggaacagt atactagcca ttctgagacg cagtggggcc aagtgcctct cactttggct  12240
ttctcctggc cagggctctt catcagggac tctcacttac aacctttaac tcttccccat  12300
ctgatcagaa cacacaaaag acactgatgc tctattagca tagggcttcc atccccatga  12360
tgccttgttc tccaggcctt cattcttcta atggcagcca tcactaccaa gcttgcctcc  12420
cacttgcgta ctgttttcc caacagccta tttgacctgc aacagctaga gccaccctt  12480
gaaaacacac caggggctgg agagctgact cagttggtaa gagcactggc tgctcttcca  12540
cagggcaggg ttcaagtaat agcaactacg tggtggctca caaggcaac ttcagcttca  12600
gaggatatgc tgccctcttc tggctgatgc aggcactgca ctcacagagt gcacagacat  12660
gcagaaaagg caaaacaccc aatatacaac cacaaaacaa actgtatccc gtcctttctc  12720
agtaccccat gccatgccca gtctccatgg catcctccta aacacacaat gaaattccag  12780
tttctgactt ggagttatga ggctctgtgg aacctggccc aagctcatcc ctcgctccct  12840
ctgttccaga tacttctgct agctcttaga gcccagctgg ttctacctca gagtcttcgt  12900
gcctgcaggt gcctctgccc agaacatatt tccacccgga tcctccccaa ggctgactgt  12960
tgcttgtatc cagagtcggt tcagagaggc ctgcctccct ttaccaagac tccactttga  13020
acaaagtgct aagtcttcct ggcattattt tgtgtttgct catttaaaat ttgtttgctg  13080
ttccttctct gctatccctg gaaaacagcg tcaatgagag caaggatttt ttttttccct  13140
atcccctgga accagcctgc acacagtgga ccttctattt aaagaaatgg caagtagggt  13200
gtgggtgtgc ctttaattcc agaactcaga aggcagaggt aggtggatct ttgtgtgctg  13260
ggagccaccc tggtctatag agtgagttcc aggacagcca aagctattca gagacaccct  13320
atctagaaaa tcctggggag gggggagag tggttactta tgactgggta acagtctaag  13380
gacacatgaa gacaaccctg ccagccccc aatgccctca tctaaacagt actccctccc  13440
cttccacctt tgtcctgaca gtttctgcc aggccagcat tcagtctcct tcccctggc  13500
ctagaaagaa cacatcatag aaatgtcctc caaccagcca ccagcccagc tccagggccc  13560
tgggcagtgg ggggagacaa gtctagaaga acatctcccc cacagtggtc acccagctga  13620
ggccctcccc tgggccagtc cgttgcctag gcaatggctc tctgaggagc agctggtatt  13680
aactctttga taaccagggt cagcagctcg ccctatgaca ggggaaaggt cccgtgggat  13740
gagctatgag acagcctttc gtggtcctac aatactgaac tctttagagt agtggtgagc  13800
tggagaggca ggaggagcaa acgggctgct ggagtcacag ggacagaaag tagaaggcac  13860
aaaacatcag ccacctgccc cattcctggg agcaaagcat ccccaggttc ctacacccac  13920
cacctaggta ggctctagtt ctgggctgaa agaggaacca gccagcaggc cctacaggcc  13980
cccattgccc tctgctgtgc ttggatgatc agttcatagc ctttagagta gaatgacctc  14040
atgcgataga aaggagaaaa ggctgtgcct cggatcctgg ttttcctgct tattcgtctt  14100
ggttaatgtt tagctttgga tttcctcaca tgatgtcctt gccaaggctg caaaagcctc  14160
aggtttcaag cccacatgta ctgctccagc aggtccacct ctatggccct ctcggtgcag  14220
atcgcccacc ccatccgagg ctctgttatt tcttctcaga attggtaaat ctctgaaaac  14280
atcttagttg attatggctt gtcatctctt gttatcttaa gagaggagat gttttctttt  14340
ctgtcttgtt cactttaaga gctccaagct tggggctaga gagatggctc agcagttaag  14400
agcatggtct gtgcttccag aagttccagg ttcaattccc agcaccaaca tggcagttca  14460
```

-continued

```
caactgtcta taagttccag gagatccaac accttcagac agatatgtgt gtgtacgtgt    14520
gtgtgcatac atacatacat acatacatac atacatacat acagggaaaa caccaatgca    14580
cattacatga aagttaagaa agaaagaact tcaagcttaa aaacggcagg cctggaagct    14640
gtttgaggat aggttccggc aaaactaggg tgaaaccaaa aaagatgttg gggtgacagt    14700
gtctctgacc acgggaggcc gcaaaggggg gtttcatgct gattgctgca cagcacatag    14760
tcatggctgg aagtggaata atctagaaga gtttcttcta ggaagaaaaa taacaccaca    14820
ggctccatat gatgagcaag actgagatcc tgaataaacg caaaccttgc caggcacatt    14880
attctctggg aaatagtaaa ctaaacaaag tcaacgagta aggtctggaa atgctttaac    14940
acagggcagt ttagtataag aaaagacacc catttggtct tgcaaaggcc attctccctg    15000
gcgtcaagag agcagacagc agaacagaag aacccagcac aggcctagca cactgcttgg    15060
ccctcaggaa acagtgcttg cctaacagtt actgagcacc tgtgtgctgg ataaggctct    15120
gtgagctctg cactcaatgt gtctgagtac atgtgatagt cgctcccatt tttcagaccg    15180
cgaaagtgag gcataatata ctagaccagt tttctgaggt cagtataaga gctggattca    15240
cacccaggtt cgcaatctcc ttgccagggc tagctctaga agccacacca tccatcttca    15300
gggccttctt gccaaagagc agacgctagc accacataca tatgtgcacg acctgtcctg    15360
gaaactgggc tgcaaagcca cagggctgca gttctgaccc attccgggga gctgaacggt    15420
gaggccagag cagggcttac cttcctgcag tctttgcaga atacggagga gctgcccagg    15480
aatcccagca cctccccgca gagcagacac tgggagagac cgttgcccat cacgttcctc    15540
tgcattgtct ccagccgctc caccagccgc ctgcagcaca ggacagggcg tcagagggaa    15600
ggtgcttcag aggactgcag tgggagtcta agcatacacg ctcacctcac ctcgcccctt    15660
cccctggctg actcccagtc actggttaac ttgctgttaa cagagcagct cgggtgttgc    15720
tgcacactgg aaatagtgta actaataggc cggatacaca catggccccg gctctcttgg    15780
aatttaggtt caacaaagag gaagattcat gaacaagaaa acaagccaag agtgagggga    15840
caagaagggc cagataaggc gaggtcagtg gaggcctggg aagacacttt gaagacatgc    15900
gacagggtgc tgagcaatgt cccatatgcc agagaagggc ccgtggctaa ggcagatctc    15960
agaggtttat aggtcacagg ccggaggctc atttcaatct ggagtcactg gagagtttga    16020
aggcgattgg atttacgtga cattttttcta agctcctgtg gaaatctgga agaatgagga    16080
gagaggaaag gaagaagcca ggaggacgtg ggaccctctc tccaaagcag gctggaggtc    16140
tcgaactgcg tcccagaggg cagtactgaa agtctggtag gctttggggc agagcatctg    16200
ggcagatgag aagctggcaa cagaagagaa aaatcaactc ttctttgaga ctgccggatg    16260
ctgagcacac aggaacccag ctgagcctgc acaggtgccc ggcctgggat cgatagccct    16320
tcccactgga gatgccctct ccaccctcca cctcctgcta tataaccaac tgtttggttt    16380
gtcagtcact ctgcttctgg tacccagcgg atattcagta agaactcttg aatggatgca    16440
gagtagcgtg tggccacatc agcccctccc atggggaaag gagccacgct tcctgcttta    16500
gaggggactg gagctgggga aacaggaagt gacttgctga gggatgaagc tcccaagaag    16560
tagagcctgg gtccccactt ctaaacttgc ctagtatggg gatccccca ggctctcact    16620
ttcctgaggc aacaggctgt tgctaagggg gacaagggat agttagctca tcagtgaagc    16680
tacttcctcc tgcatgctat gcggtgaaca cttccatttt ccacacattg acaccgctgt    16740
ccatctgtag ggcttggggg caaacccagt tctagcccag tgtggctcgg ttgcccccag    16800
```

-continued

| | |
|---|---|
| gaaccccctg tcagtccatg tcattttcca cacatcatgt aggacatgct tcctttgtgt | 16860 |
| gaacaattac tgtttctggg tccatctatt ccctgctgct cggggcaggg tgtcatcaga | 16920 |
| tcacagaaag gacttcctga ggcagcactg ggacagcagc ctgctgactg agggtgtcca | 16980 |
| aaagcgcttc caccaaggct cgtgcaaccc actccctgct caccatcctg ggtatggggc | 17040 |
| acagagtagg ggtgtgtgtt gggggagggg tggttgtcga tcaccagcat tcaaggttag | 17100 |
| cccagaacct ggccaggccc ttggggagga gatctgtaag aagccaggct agatgggggg | 17160 |
| ggaaaaaaaa gaaaaaccca gccgttctgc catgagccct gtttgtactg acaagataat | 17220 |
| gacctgtctg tatgattgag gctcatacaa gaggccgttg acgcagcagt catctttcta | 17280 |
| gtgggggcat cgcctcctaa agctgccttt ctgctgtgtc tgacttttaa aaatgatca | 17340 |
| tgaaactaat gggaaaagat gagcagaaaa ataacgagat cagaacgagc tgagttccta | 17400 |
| cgcaaagcag ccgaacccag tacagccaag ctcccctatc tgagcttgtc caaatcaacc | 17460 |
| tacgacagga aaaaggcaca cgccatcatg ttggatggcc cagccctgga tgtgagagac | 17520 |
| caggagagaa gctgaaaacc cactggaggg cgcctcctgt tggggcctca ggtggggggc | 17580 |
| caattcactg accagtcagt ctcctcttga gtccattcct tgcctgagct gcaggaggat | 17640 |
| actcagagcc caaatccaaa atgctcctgg gctcactatt ccctgcacac ctgtctgggg | 17700 |
| tcttgaatca atgccatccc cagctcacag ctgcctacat cccagagggg ggcaatgaga | 17760 |
| agctggggcc agcctgactc tttgcagacc agcccctgc agactccctg ctcagtgccc | 17820 |
| ggactctgct tacccaattc tctgctgctc caggatgtct agcctctctg ctctctggat | 17880 |
| gacctgaagg atgatctcca gctctccggg gctcaggcac tggctcctcc tctgcttctc | 17940 |
| cgtctggtac gtgtgcacag accagcccgt ctgcagcctt gggagagaat agtatggttg | 18000 |
| gaggtaagac gacagcccac gacagccgta acccagtgta cccacaaagc ccttgtcaga | 18060 |
| gtgctgcagc acagcctgga cactgtggtc catgataaac gttctagat ggtttgtgta | 18120 |
| tgtatccatc actgagtgtc attgctagag ggcaatgtgg gacccacagt tttcctgtct | 18180 |
| agaaggaatg tcacggagag ccaggcccta ctctgactgg tcctctcttg gccttttaca | 18240 |
| ctgtgtaccc ttcacactct gcacttaaac cataccagcc ttttgttagg attctctgta | 18300 |
| tgctatgttc cttctacccc agggcctttg cacatgctgt tttgtatgct tagaactttc | 18360 |
| tccatatttc catgtaacat ttacctctct gagtcaagag aagaatcata gaagaatcat | 18420 |
| gtaaaagaag gtcttggtcc ctgacccagt taataccca cccctaccta ctgccaatca | 18480 |
| tcatcaacaa cagaattcac atctttaagt atccatacaa ctttgacctc tccccatctc | 18540 |
| tgctttaata tgaaagacca attgagttta ggtatgtgga gagacacctg ggtgcttgga | 18600 |
| aggaagaatg tgggttggaa aactctctgt gtttcctagg gggtctactg gactcgatgt | 18660 |
| ctagctctgc aacgggcatc tgtctctcag acacacacct gggaggagac acactggctc | 18720 |
| ttctgagagg ctaggacagc ttcagcagct ggtgaatgag agacaaagtt gggaatgaag | 18780 |
| gggatgctgg aaggtcaagg gacagctggg ctcttggacg aggtccaaga gctgaggtct | 18840 |
| cccagcaatg tgcaccctgc cagagagggc acctaattgg cctggcatca gagatggtga | 18900 |
| gtgggaccaa tctcatccct agtcattctc tctgcagggg tgaggtgggg gggggctga | 18960 |
| ggcacccaga tggaggagag caaggatgct cacacatcac atgcgacgcc attcttcctg | 19020 |
| agcgtttcag atggattttt ctatccacct ttgatgtctc agctctgact cccacaggct | 19080 |
| tctaacgtct aattgcgaat ttcttaagct tggtcccagt tgggaaatgc tggcttctga | 19140 |
| tgccaacaca gtctgatagc tgcagggatg ttcttgtcct atcagagcca gggatggcac | 19200 |

| | |
|---|---:|
| ccaccagaga tctggaacag actagagggc atgaggggca tctgagaggc tcagccacag | 19260 |
| ggacactgtg tgtgtgtgtg tgtgtgtgtg tgtgtgtgtg tgtgtcgggg gggggggcag | 19320 |
| gccaggccca accaaaattg aagggtcact agtctgaggg gtaataggaa aatgaagacc | 19380 |
| tccaaaaaga cacaagggaa tcacagaagg acacagaccc cactaaggac gtaggaaaga | 19440 |
| tgctgtagcc agcggtggtc tctactgaag tgagctgttc attcagggaa caggcatgtg | 19500 |
| ctctgtattg cccctctatg ccaggctcag ggacaagagc aggcccaatg gggaagtctt | 19560 |
| gctccctgtg ggctgttgtg aaagagcaca ggtgtgggag tcagctggac ttggatgtag | 19620 |
| gttccagccc agccactgac aagggacacg gcaaggagt gaaggcctca ttttccttat | 19680 |
| ctgagaaatg ggaacatgtt agttcgtggt gagtaataca taagcatggg ccgagagtgg | 19740 |
| tgtgcatttg acatccgcct ctctccaaac tcctccctgg ggagcaaaac ttgcaaaaga | 19800 |
| ctgggaagag gggaagaggg cagcaggtgg agagggaggg aagggccact cctgcaggcc | 19860 |
| acagatgctt acttggctct cagagcaagc tgccgatcgt tggggcaaac ccactgatca | 19920 |
| tttccactgc tgaagatggt gtcagccatg acggggagca cagcccaggg caggagtcac | 19980 |
| atctgaggca ggaggacaag ggaagcacat gttagtgact ggggtgttga cgggaatccc | 20040 |
| gatccctgct gaccattgat gctacactct ttttttttaag gttttcgag acagggtttc | 20100 |
| tctgtgtagc cctggctgta gtagaccagg ctgtccttga actcagaaat cctcctgcct | 20160 |
| ctgcctccca agtgctggga ttaaaggcat gcaccaccac tgcctggcga tgctacactc | 20220 |
| ttaactcctc cagcaaaagc cttactcaga gctccttttc caaaggctcg ggatcttggg | 20280 |
| acaggtggct aggtgcatca catcgctaag tgaccagagt agacaatgac atcagagggt | 20340 |
| gagaatcaga agggagagaa ggcaccatct cagcaacttt caactcagct ggcaagccct | 20400 |
| gcagagcatc agcttctgcc ctttcccaca cagccccact gccctgagaa catcccaaag | 20460 |
| agagacacag gcaagctcat gagtcccctc aa | 20492 |

<210> SEQ ID NO 3
<211> LENGTH: 1091
<212> TYPE: DNA
<213> ORGANISM: Mus musculus

<400> SEQUENCE: 3

| | |
|---|---:|
| ccatggagac tgggcatggc atggggtact gagaaaggac gggatacagt ttgttttgtg | 60 |
| gttgtatatt gggtgttttg ccttttctgc atgtctgtgc actctgtgag tgcagtgcct | 120 |
| gcatcagcca gaagagggca gcatatcctc tgaagctgaa gttgcccttg tgagccacca | 180 |
| cgtagttgct attacttgaa ccctgccctg tggaagagca gccagtgctc ttaccaactg | 240 |
| agtcagctct ccagcccctg gtgtgttttc aagggtggc tctagctgtt gcaggtcaaa | 300 |
| taggctgttg ggaaaaacag tacgcaagtg ggaggcaagc ttggtagtga tggctgccat | 360 |
| tagaagaatg aaggcctgga gaacaaggca tcatggggat ggaagcccta tgctaataga | 420 |
| gcatcagtgt cttttgtgtg ttctgatcag atggggaaga gttaaaggtt gtaagtgaga | 480 |
| gtccctgatg aagagccctg gccaggagaa agccaaagtg agaggcactt ggccccactg | 540 |
| cgtctcagaa tggctagtat actgttccca cactagccct gggaagttcc tgtgactcct | 600 |
| gcctgcctgc ctgcctgtgg acacaaattg aagggtgttt ctctcttcct cgaagcagga | 660 |
| acagaggtac agaggtaccc acagctgtag gaccggcttg ggtcccgttc ccatattgct | 720 |
| tctgtggagg gctctggtaa aactcactcc gcctctctcc gccttcattc ctttatctgt | 780 |

```
aagacaaggt cgaaaggcag ccatcagcac caggtggatg tgagggatgg attagctgat    840
gcaaggaagc ccttcacagc ctgctccatc actagctcct agcaaaggca ggggcaccct    900
gtcactgtca tggtgaccgg ccacccccag gggctccctg ctcagaggtt tgccacagag    960
catggacccg accatcatga tcacaggaga cacagagcga ggcacagatc agccagccgg   1020
ggcaagatgc cctaacaacc ctttatttat ttccctgtgg tttgtgactg ggaagtccaa   1080
ggcaagtcga c                                                        1091
```

<210> SEQ ID NO 4
<211> LENGTH: 994
<212> TYPE: DNA
<213> ORGANISM: Mus musculus

<400> SEQUENCE: 4

```
cgaagcagat gtgactcctg ccctgggctg tgctccccgt catggctgac accatcttca     60
gcagtggaaa tgatcagtgg gtttgcccca acgatcggca gcttgctctg agagccaagc    120
tgcagacggg ctggtctgtg cacacgtacc agacggagaa gcagaggagg agccagtgcc    180
tgagccccgg agagctggag atcatccttc aggtcatcca gagagcagag aggctagaca    240
tcctggagca gcagagaatt gggcggctgg tgagcggct gagacaatg cagaggaacg    300 tgatgggcaa cggtctctcc cagtgtctgc tctgcgggga ggtgctggga ttcctgggca    360
gctcctccgt attctgcaaa gactgcagga agaaagtctg caccaagtgt gggatcgagg    420
cttcccccgg ccagaagcgg cccctgtggc tgtgtaagat ctgcagtgag cagagagagg    480
tctggaagag gtcaggggcc tggttctaca agggctccc caagtacatc ttgcccctga    540
aaacccctgg ccgggctgat gatccccact tccgacctct gcctgtggag cccacagaaa    600
cacagcctcc gagtgctgaa accagccgtg tctacacatg ggcccgaggg agagtggttt    660
ccagtgacag tgacagtgac tcagatctca gctcctccag cctggaggac agacccttgc    720
cctctggggt caagggcaca aaaggtgaca agcctagagg ggactcaggt gccagcatgg    780
agtcacccag gctggggcct gcccgtccac ccagccatct ctcgggcagt cagagcagcc    840
taggcagtga ggctgggaca ggtgctacag agccacaggg aggcacccca gcccagcctg    900
agcccagggt acccggcaaa agacacacat gggcaactcc ccgctactga agtggccagc    960
tgacatctcc aggctgaggc aaactcttcc agaa                                994
```

<210> SEQ ID NO 5
<211> LENGTH: 20
<212> TYPE: DNA
<213> ORGANISM: Mus musculus

<400> SEQUENCE: 5

```
cgaagcagat gtgactcctg                                                 20
```

<210> SEQ ID NO 6
<211> LENGTH: 20
<212> TYPE: DNA
<213> ORGANISM: Mus musculus

<400> SEQUENCE: 6

```
ttctggaaga gtttgcctca                                                 20
```

<210> SEQ ID NO 7
<211> LENGTH: 20
<212> TYPE: DNA
<213> ORGANISM: Mus musculus

```
<400> SEQUENCE: 7
gcagtggaaa tgatcagtgg                                              20

<210> SEQ ID NO 8
<211> LENGTH: 20
<212> TYPE: DNA
<213> ORGANISM: Mus musculus

<400> SEQUENCE: 8
catcacgttc ctctgcattg                                              20
```